(12) United States Patent
Machielse et al.

(10) Patent No.: US 9,492,545 B2
(45) Date of Patent: Nov. 15, 2016

(54) COMPOSITIONS OF STATINS AND OMEGA-3 FATTY ACIDS

(71) Applicant: Omthera Pharmaceuticals, Inc., Princeton, NJ (US)

(72) Inventors: Bernardus Nicolaas Machielse, North Potomac, MD (US); Timothy J. Maines, Potomac, MD (US); Michael H. Davidson, Highland Park, IL (US); Bharat M. Mehta, Mendham, NJ (US)

(73) Assignee: Omthera Pharmaceuticals Inc., Princeton, NJ (US)

( * ) Notice: Subject to any disclaimer, the term of this patent is extended or adjusted under 35 U.S.C. 154(b) by 0 days.

(21) Appl. No.: 14/399,355

(22) PCT Filed: May 7, 2013

(86) PCT No.: PCT/US2013/039972
§ 371 (c)(1),
(2) Date: Nov. 6, 2014

(87) PCT Pub. No.: WO2013/169797
PCT Pub. Date: Nov. 14, 2013

(65) Prior Publication Data
US 2015/0104504 A1    Apr. 16, 2015

Related U.S. Application Data

(60) Provisional application No. 61/643,764, filed on May 7, 2012.

(51) Int. Cl.
*A61K 47/12* (2006.01)
*A61K 31/55* (2006.01)
(Continued)

(52) U.S. Cl.
CPC ............. *A61K 47/12* (2013.01); *A61K 9/4825* (2013.01); *A61K 9/4891* (2013.01);
(Continued)

(58) Field of Classification Search
CPC .. A61K 31/202; A61K 31/22; A61K 31/366; A61K 31/40; A61K 31/405; A61K 31/47; A61K 31/505; A61K 47/12; A61K 9/4825; A61K 9/4891; A61K 2300/00; A61K 31/55
See application file for complete search history.

(56) References Cited

U.S. PATENT DOCUMENTS 4,377,526 A   3/1983 Fujita et al.
5,106,542 A   4/1992 Traitler et al.
(Continued)

FOREIGN PATENT DOCUMENTS

BR   PI8803255 A   2/1990
CN   102311868 A   1/2012
(Continued)

OTHER PUBLICATIONS

Davidson et al., 1997, "Separate and Joint Effects of Marine Oil and Simvastatin in Patients With Combined Hyperlipidemia," *Am J Cardiol* 80:797-798.
(Continued)

*Primary Examiner* — Aradhana Sasan
(74) *Attorney, Agent, or Firm* — Dechert LLP

(57) ABSTRACT

The present disclosure provides pharmaceutical compositions of statins and polyunsaturated fatty acids (PUFAs), in which the statins are dissolved in the PUFAs, the PUFA species being present substantially in the free acid form. Also provided are oral unit dosage forms of the disclosed pharmaceutical compositions and methods of treating blood lipid disorders using the compositions and oral unit dosage forms.

32 Claims, 2 Drawing Sheets

Figure 1:
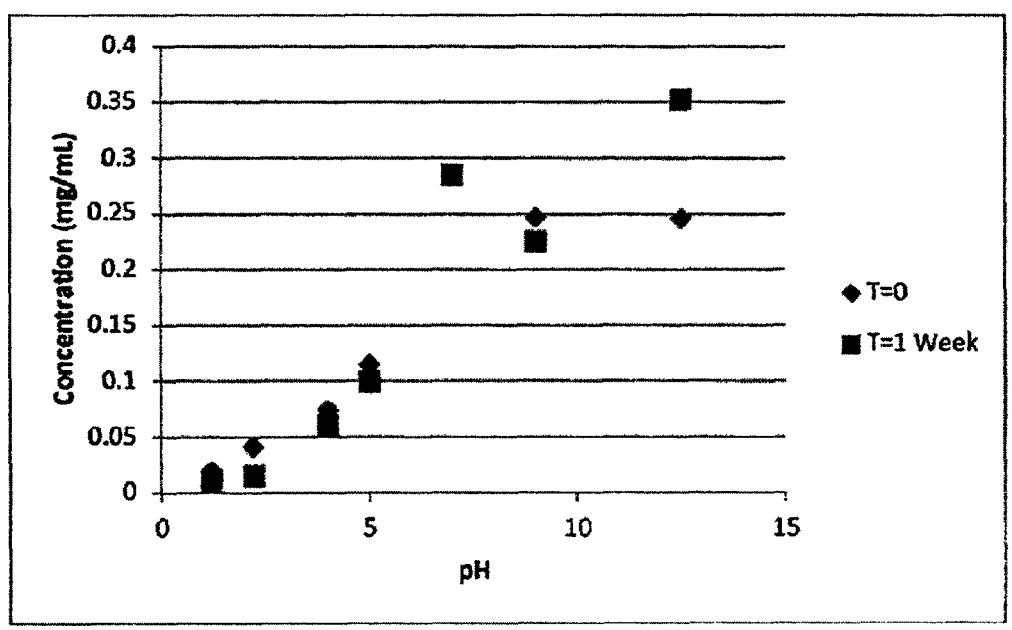

(51) Int. Cl.
*A61K 31/202* (2006.01)
*A61K 9/48* (2006.01)
*A61K 31/405* (2006.01)
*A61K 31/47* (2006.01)
*A61K 31/505* (2006.01)
*A61K 31/22* (2006.01)
*A61K 31/40* (2006.01)
*A61K 31/366* (2006.01)

(52) U.S. Cl.
CPC ............ *A61K 31/202* (2013.01); *A61K 31/22* (2013.01); *A61K 31/366* (2013.01); *A61K 31/40* (2013.01); *A61K 31/405* (2013.01); *A61K 31/47* (2013.01); *A61K 31/505* (2013.01); *A61K 31/55* (2013.01)

(56) References Cited

U.S. PATENT DOCUMENTS

| | | |
|---|---|---|
| 5,243,046 A | 9/1993 | Traitler et al. |
| 5,502,077 A | 3/1996 | Breivik et al. |
| 5,661,180 A | 8/1997 | DeMichele et al. |
| 5,679,809 A | 10/1997 | Bertoli et al. |
| 5,792,795 A | 8/1998 | Buser et al. |
| 5,886,037 A | 3/1999 | Klor et al. |
| 5,945,318 A | 8/1999 | Breivik et al. |
| 5,948,818 A | 9/1999 | Buser et al. |
| 6,284,268 B1 | 9/2001 | Mishra et al. |
| 6,326,355 B1 | 12/2001 | Abbruzzese et al. |
| 6,479,544 B1 | 11/2002 | Horrobin |
| 6,528,699 B1 | 3/2003 | Meade et al. |
| 6,664,405 B2 | 12/2003 | Lee |
| 7,112,609 B2 | 9/2006 | Hermelin et al. |
| 7,485,323 B2 | 2/2009 | Dolphin et al. |
| 7,541,480 B2 | 6/2009 | Bruzzese |
| 7,642,287 B2 | 1/2010 | Guzman et al. |
| 7,709,668 B2 | 5/2010 | Catchpole et al. |
| 7,960,370 B2 | 6/2011 | Sachetto et al. |
| 8,003,813 B2 | 8/2011 | Wanasundara et al. |
| 8,613,945 B2 | 12/2013 | Manku et al. |
| 8,663,662 B2 | 3/2014 | Manku et al. |
| 9,050,308 B2 | 6/2015 | Maines et al. |
| 9,050,309 B2 | 6/2015 | Maines et al. |
| 2002/0025983 A1 | 2/2002 | Horrobin |
| 2004/0106591 A1 | 6/2004 | Pacioretty et al. |
| 2004/0236128 A1 | 11/2004 | Rubin |
| 2005/0267197 A1 | 12/2005 | Berlin |
| 2006/0088596 A1 | 4/2006 | Labrecque |
| 2006/0211762 A1 | 9/2006 | Rongen et al. |
| 2006/0211763 A1 | 9/2006 | Fawzy et al. |
| 2006/0229461 A1 | 10/2006 | Sung et al. |
| 2007/0020340 A1 | 1/2007 | Rubin et al. |
| 2007/0071176 A1 | 3/2007 | Main |
| 2007/0212411 A1 | 9/2007 | Fawzy et al. |
| 2007/0265341 A1 | 11/2007 | Dana et al. |
| 2008/0107791 A1 | 5/2008 | Fichtali et al. |
| 2008/0299187 A1 | 12/2008 | Opheim |
| 2009/0182049 A1 | 7/2009 | Opheim |
| 2010/0160435 A1 | 6/2010 | Bruzzese |
| 2011/0034555 A1 | 2/2011 | Osterloh et al. |
| 2011/0071176 A1 | 3/2011 | Rowe |
| 2011/0097394 A1 | 4/2011 | Sachetto et al. |
| 2011/0117180 A1 | 5/2011 | Yan et al. |
| 2011/0268770 A1 | 11/2011 | Seternes et al. |
| 2011/0294841 A1 | 12/2011 | Guzman et al. |
| 2012/0121698 A1 | 5/2012 | Manku et al. |
| 2012/0157530 A1 | 6/2012 | Manku et al. |
| 2012/0157531 A1 | 6/2012 | Osterloh et al. |
| 2012/0252850 A1 | 10/2012 | Milne et al. |
| 2012/0321602 A1 | 12/2012 | Rosedale |
| 2013/0095178 A1 | 4/2013 | Manku |
| 2013/0177643 A1 | 7/2013 | Maines et al. |
| 2013/0209556 A1 | 8/2013 | Maines et al. |
| 2013/0295173 A1* | 11/2013 | Machielse ............ A61K 31/505 424/463 |
| 2014/0017306 A1 | 1/2014 | Manku et al. |
| 2014/0080909 A1 | 3/2014 | Manku et al. |
| 2014/0088194 A1 | 3/2014 | Manku et al. |
| 2014/0094520 A1 | 4/2014 | Bobotas et al. |
| 2014/0100272 A1 | 4/2014 | Bobotas et al. |
| 2014/0100273 A1 | 4/2014 | Bobotas et al. |
| 2014/0100274 A1 | 4/2014 | Bobotas et al. |
| 2014/0100275 A1 | 4/2014 | Bobotas et al. |
| 2014/0100281 A1 | 4/2014 | Bobotas et al. |
| 2014/0107198 A1 | 4/2014 | Bobotas et al. |
| 2014/0107199 A1 | 4/2014 | Fawzy et al. |
| 2014/0107200 A1 | 4/2014 | Fawzy et al. |
| 2014/0107205 A1 | 4/2014 | Bobotas et al. |
| 2014/0107206 A1 | 4/2014 | Fawzy et al. |
| 2014/0154310 A1 | 6/2014 | Osterloh et al. |
| 2014/0155455 A1 | 6/2014 | Osterloh et al. |
| 2014/0194512 A1 | 7/2014 | Fawzy et al. |
| 2014/0249226 A1 | 9/2014 | Bobotas et al. |
| 2015/0004224 A1 | 1/2015 | Maines et al. |

FOREIGN PATENT DOCUMENTS

| | | |
|---|---|---|
| DE | 10214005 A1 | 10/2003 |
| DE | 102006008030 A1 | 8/2007 |
| EP | 0 289 204 | 2/1988 |
| EP | 302481 A2 | 2/1989 |
| EP | 302482 A2 | 2/1989 |
| EP | 0347509 A1 | 12/1989 |
| EP | 0 825 858 | 3/1998 |
| EP | 1106072 A1 | 6/2001 |
| EP | 1 202 950 | 9/2003 |
| EP | 1352648 A1 | 10/2003 |
| EP | 1 755 565 | 2/2007 |
| EP | 1 803 440 A1 | 7/2007 |
| EP | 2 455 070 A1 | 5/2012 |
| FR | 2896172 B1 | 10/2008 |
| GB | 2033745 B | 5/1980 |
| GB | 2 090 529 | 7/1982 |
| GB | 2 223 943 | 4/1990 |
| GB | 2300807 A | 11/1996 |
| JP | 59-157018 | 9/1984 |
| JP | 2001054396 A | 2/2001 |
| KR | 100684641 B1 | 2/2007 |
| WO | WO-90/04391 | 5/1990 |
| WO | WO-95/09622 A1 | 4/1995 |
| WO | WO-95/22901 A1 | 8/1995 |
| WO | WO-97/39759 A2 | 10/1997 |
| WO | WO-00/49117 A1 | 8/2000 |
| WO | WO-01/06983 A2 | 2/2001 |
| WO | WO-01/15552 A1 | 3/2001 |
| WO | WO-01/49282 A2 | 7/2001 |
| WO | WO-02/10322 A1 | 2/2002 |
| WO | WO-02/102394 A2 | 12/2002 |
| WO | WO-03/072111 A2 | 9/2003 |
| WO | WO-03/072784 A1 | 9/2003 |
| WO | WO-03/082339 A1 | 10/2003 |
| WO | WO-2004/043894 A1 | 5/2004 |
| WO | WO-2004/056370 A1 | 7/2004 |
| WO | WO-2004/098311 A1 | 11/2004 |
| WO | WO-2005/025334 A1 | 3/2005 |
| WO | WO-2005/060954 A1 | 7/2005 |
| WO | WO-2005/079853 | 9/2005 |
| WO | WO-2005/123060 | 12/2005 |
| WO | WO-2005/123061 A1 | 12/2005 |
| WO | WO-2006/004438 A1 | 1/2006 |
| WO | WO-2006/017692 A1 | 2/2006 |
| WO | WO 2006/017698 A2 | 2/2006 |
| WO | WO 2006/045865 A1 | 5/2006 |
| WO | WO-2006/069668 A1 | 7/2006 |
| WO | WO-2006/077495 A1 | 7/2006 |
| WO | WO-2006/088418 A1 | 8/2006 |
| WO | WO-2006/100241 A2 | 9/2006 |
| WO | WO-2006/102896 A2 | 10/2006 |
| WO | WO-2006/117664 A1 | 11/2006 |
| WO | WO-2006/117668 A1 | 11/2006 |
| WO | WO-2007/017240 A2 | 2/2007 |
| WO | WO-2007/019373 A1 | 2/2007 |
| WO | WO-2007/096387 A1 | 8/2007 |
| WO | WO-2007/128801 A1 | 11/2007 |

(56) References Cited

FOREIGN PATENT DOCUMENTS

| WO | WO-2007/130713 A1 | 11/2007 | | |
|---|---|---|---|---|
| WO | WO-2007/130714 A1 | 11/2007 | | |
| WO | WO-2008/000731 A1 | 1/2008 | | |
| WO | WO 2008/000731 A2 | 1/2008 | | |
| WO | WO 2008/045170 A2 | 4/2008 | | |
| WO | WO-2008/088808 A1 | 7/2008 | | |
| WO | WO-2008/103753 A2 | 8/2008 | | |
| WO | WO-2008/113177 A1 | 9/2008 | | |
| WO | WO-2008/133573 A1 | 11/2008 | | |
| WO | WO-2009-009040 A2 | 1/2009 | | |
| WO | WO-2009/014452 A1 | 1/2009 | | |
| WO | WO-2009/017102 A1 | 2/2009 | | |
| WO | WO-2009/020406 A1 | 2/2009 | | |
| WO | WO-2009/028457 A1 | 3/2009 | | |
| WO | WO-2009/040676 A2 | 4/2009 | | |
| WO | WO 2009/059717 A2 | 5/2009 | | |
| WO | WO-2009/065395 A2 | 5/2009 | | |
| WO | WO-2009/139641 A1 | 11/2009 | | |
| WO | WO-2010/029433 A1 | 3/2010 | | |
| WO | WO-2010/039030 A1 | 4/2010 | | |
| WO | WO 2010/041017 A2 | 4/2010 | | |
| WO | WO-2010/049954 A1 | 5/2010 | | |
| WO | WO 2010/069951 A1 | 6/2010 | | |
| WO | WO-2010/103402 A1 | 9/2010 | | |
| WO | WO-2010/118761 A1 | 10/2010 | | |
| WO | WO-2010-119319 A1 | 10/2010 | | |
| WO | WO-2011-048493 A1 | 4/2011 | | |
| WO | WO 2011/068923 A1 | 6/2011 | | |
| WO | WO 2011/078712 A1 | 6/2011 | | |
| WO | WO-2011/095284 A1 | 8/2011 | | |
| WO | WO-2011/128626 A1 | 10/2011 | | |
| WO | WO-2011/133610 A1 | 10/2011 | | |
| WO | WO-2011/161702 A1 | 12/2011 | | |
| WO | WO-2012/032415 A2 | 3/2012 | | |
| WO | WO 2012/032415 A2 | * | 3/2012 | ............... A61K 9/10 |
| WO | WO 2012/032417 A2 | 3/2012 | | |
| WO | WO-2012/038833 A1 | 3/2012 | | |
| WO | WO-2012/087153 A1 | 6/2012 | | |
| WO | WO-2012/095525 A1 | 7/2012 | | |
| WO | WO 2012/104655 A2 | 8/2012 | | |
| WO | WO-2012/112511 A1 | 8/2012 | | |
| WO | WO-2012-112517 A1 | 8/2012 | | |
| WO | WO-2012/112520 A1 | 8/2012 | | |
| WO | WO-2012-112527 A1 | 8/2012 | | |
| WO | WO-2012/112531 A1 | 8/2012 | | |
| WO | WO-2012/112902 A1 | 8/2012 | | |
| WO | WO-2012/156986 A1 | 11/2012 | | |
| WO | WO-2013/040507 | 3/2013 | | |
| WO | WO-2013/059669 | 4/2013 | | |
| WO | WO-2013/103902 | 7/2013 | | |
| WO | WO-2013/192109 A1 | 12/2013 | | |

OTHER PUBLICATIONS

Kang et al., 2004, "Development of self-microemulsifying drug delivery systems (SMEDDS) for oral bioavailability enhancement of simvastatin in beagle dogs," *International Journal of Pharmaceutics* 274 (2004) 65-73.

Nakamura et al., 1999, "Joint effects of HMG-CoA reductase inhibitors and eicosapentaenoic acids on serum lipid profile and plasma fatty acid concentrations in patients with hyperlipidemia," *Int. J. Clin. Lab Res.* 29:22-25.

PCT International Search Report from PCT/US2013/039972 date mailed Oct. 22, 2013.

1991, "Eudragit® NE Aqueous acrylic polymer dispersion," *Röhm Pharma GMBH Weiterstadt* data sheet (INFO NED-2/e) 1-2.

1994, "Eudragit® Acrylic Polymers International Availability and Acceptability for their Use in Drug Manufacture," *Rohm* 1-2.

1999, "Adis R&D Profile Purepa®," *Drugs R&D* 3:268-269.

2002, "Third Report of the National Cholesterol Education Program (NCEP) Expert Panel on Detection, Evaluation, and Treatment of High Blood Cholesterol in Adults (Adult Treatment Panel III) Final Report," *National Institutes of Health (National Heart, Lung, and Blood Institute)* (updated 2004) 1-200.

2002, "Third Report of the National Cholesterol Education Program (NCEP) Expert Panel on Detection, Evaluation, and Treatment of High Blood Cholesterol in Adults (Adult Treatment Panel III) Final Report," *National Institutes of Health (National Heart, Lung, and Blood Institute)* (updated 2004) 201-283.

2010, "Australian Public Assessment Report for Omega-3-acid ethyl ester 90," *Therapeutic Goods Administration* 1-134.

2011, "Omega-3-Acid Ethyl Esters," *The United States Pharmacopeial Conventions: Official Monographs* (34):3714-3716.

Anonymous, 2010, "Withdrawal Assessment Report for Ethyl Eicosapent Soft Gelatin Capsules," *European Medicines Agency* 1-22.

Bays et al., 2008, "Prescription omega-3 fatty acids and their lipid effects: physiologic mechanisms of action and clinical implications," *Expert Rev Cardiovasc Ther.* 6(3):391-409.

Bays et al., 2010, Effects of Prescription Omega-3-Acid Ethyl Esters on Non-High-Density Lipoprotein Cholesterol When Coadministered with Escalating Does of Atorvastatin *Mayo Clinic Proceedings* 85(2)122-128.

Beckermann et al., 1990, "Comparative Bioavailability of Eicosapentaenoic Acid and Docasahexaenoic Acid from Triglycerides, Free Fatty Acids and Ethyl Esters in Volunteers," *Arzneimittelforschung* Abstract 40(6)1.

Belluzzi et al., 1993, "Polyunsaturated fatty acid pattern and fish oil treatment in inflammatory bowel disease," *GUT* 34:1289.

Belluzzi et al., 1994, "Effects of New Fish Oil Derivative on Fatty Acid Phospholipid-Membrane Pattern in a Group of Crohn's Disease Patients," *Digestive Diseases and Sciences* 39(12):2589-2594.

Belluzzi et al., 1995, "New fish oil derivative for preventing clinical relapses in Crohn's disease: A double blind placebo controlled randomized trial," *Gastroenterology* 108(4)Supp 2:A781.

Belluzzi et al., 1996, "Effect of an Enteric-coated Fish-oil Preparation on Relapses in Crohn's Disease," *The New England Journal of Medicine* 334(24):1557-1560.

Belluzzi et al., 2000, "Polyunsaturated fatty acids and inflammatory bowel disease," *The American Journal of Clinical Nutrition* 71(suppl):339S-342S.

Belluzzi et al., 2002, "n-3 Fatty acids for the treatment of inflammatory bowel diseases," *Proceedings of the Nutrition Society*61:391-395.

Belluzzi et al., 2004, "Polyunsaturated fatty acids (n-3 PUFAs) and inflammatory bowel disease (IBD): pathogenesis and treatment," *European Review for Medical and Pharmacological Sciences* 8:225-229.

Bobotas et al., U.S. Appl. No. 61/660,757, filed Jun. 17, 2012 (64 pages).

Bobotas et al., U.S. Appl. No. 61/734,331, filed Dec. 6, 2012 (71 pages).

Bobotas et al., U.S. Appl. No. 61/780,948, filed Mar. 13, 2013 (76 pages).

Burns et al., 2007, "Effect of Omega-3 Fatty Acid Supplementation on the Arachidonic Acid: Eicosapentaenoic Acid Ratio," *Pharmacotherapy* 27(5):633-638.

Chan et al., 2002, "Factorial Study of the Effects of Atorvastatin and Fish Oil on Dyslipidaemia in Visceral Obesity," *European Journal of Clinical Investigation* 32(6):429-436.

Cohen et al., 2008, "Changes in the Prevalence of Abnormal Lipid Fractions Amount US Adults: Results from the National Health and Nutrition Examination Survey II, III and 1999-2006," Presented at the American Heart Association (AHA) conference. Nov. 8-12, 2008, New Orleans, LA.

Conner et al., 1993, "N-3 Fatty Acids from Fish Oil: Effects on Plasma Liporoteins and Hypertriglyceridemic Patients," *Annals new York Academy of Sciences* 683:16-34.

Davidson et al., 2009, "Effects of prescription omega-3-acid ethyl esters on lipoprotein particle concentrations, apolipoproteins AI and CIII, and lipoprotein-associated phospholipase A(2) mass in statin-treated subjects with hypertriglyceridemia," *J Clin Lipidol.* 3(5):332-40.

Davidson et al., 2011, "Bioavailability of a Single 4g Dose Epanova® (Omega-3 Free Fatty Acids) Versus Lovaza® (Omega-

(56) References Cited

OTHER PUBLICATIONS

3-Acid Ethyl Esters) When Consumed with Low-Fat and High-Fat Meals in Healthy Adults," *Drugs Affecting Lipid Metabolism (DALM) Symposium* Poster 1.
Davidson et al., 2011, "Novel developments in omega-3 fatty acid-based strategies," *Current Opinion in Lipidology* 22:437-444.
Davidson et al., 2011, "Poor Bioavailability of Ester Omega-3's On a Low-fat Diet is Significantly Improved with a Free Fatty Acid Formulation," Presentation, American Heart Association Annual Meeting 2011 (Nov. 2011).
Davidson et al., 2012, "A novel omega-3 free fatty acid formulation has dramatically improved bioavailability during a low-fat diet compared with omega-3-acid ethyl esters: The ECLIPSE (Epanova® compared to Lovaza® in a pharmacokinetic single-dose evaluation) study," *Journal of Clinical Lipidology* 6(6):1-12 (Epub Jan. 24, 2012).
Davidson et al., Abstract 18775: "Low Levels of Omega-3s In Hispanics Due to Genetic and Dietary Factors Can be Significantly Improved with a Highly Bioavailable Omega-3 Free fatty Acid Formulation," 2012 AHA Meeting.
Davidson, 2008, "Is LDL-C passed [sic] its prime? The emerging role of non-HDL, LDL-P and ApoB in CHD risk assessment," *Arterioscler Thromb Vasc Biol.* 28(9):1582-1583.
Davidson, M.H. et al., "Addition of omega-3 carboxylic acids to statin therapy in patients with persistent hypertriglyceridemia," Expert Rev. Cardiovasc. Ther. 12(9) 1-10 (2014).
Davidson, M.H. et al., "Novel developments in omega-3 fatty acid-based strategies," Current Opinion in Lipidology 2011, 22: 437-444.
Davidson, M.H., "Omega-3 fatty acids: new insights into the pharmacology and biology of docosahexaenoic acid, docosapentaenoic acid, and eicosapentaenoic acid," Curr. Opin. Lipodol. 2013, 24: 1-8.
De Caterina, 2011, "n-3 Fatty acids in cardiovascular disease," *New England Journal of Medicine* 364:2439-2450.
De Caterina, 2011, "n-3 Fatty acids in cardiovascular disease," *New England Journal of Medicine* Supplementary Appendix 1-19.
Deckelbaum et al., 2006, "n-3 Fatty acids and gene expression," *Am J Clin Nutr* 83(suppl):1520S-1525S.
Donadio et al., 2001, "A Randomized Trial of High-Dose Compared with Low-Dose Omega-3 Fatty Acids in Severe IgA Nephropathy," *J Am Soc Nephrol* 12:791-799.
Durrington et al., 2001, "An Omega-3 Polyunsaturated Fatty Acid Concentrate Administered for One Year Decreased Triglycerides in Simvastatin Treated Patients with Coronary Heart Disease and Persisting Hypertriglyceridaemia," *Heart* 85:544-548.
Dyerberg et al., 1995, "20. Bioavailability of n-3 fatty Acid Formulations," *Prevention and Treatment in Vascular Disease* Bi & Gi Publishers 217-226.
Eslick et al., 2009, "Benefits of fish oil supplementation in hyperlipidemia: a systematic review and meta-analysis," *Intn'l J. Cardiol.* 136:4-16.
Farzaneh-Far et al., 2010, "Association of Marine Omega-3 Fatty Acid Levels with Telomeric Aging in patients with Coronary Heart Disease," *JAMA* 303(3):250-257.
FDA Draft Guidance on Omega-3-Acid Ethyl Esters (Sep. 2012).
FDA Product Label for LOVAZA® 1-14 (Dec. 2010).
FDA Product Label for Omacor (Nov. 10, 2004).
FDA Product Label for VASCEPA™ 1-12 (Jul. 2012).
Feagan et al., 2008, "Omega-3 Free Fatty Acids for the Maintenance of Remission in Crohn disease: The EPIC Randomized Controlled Trials," *Original Contribution* 299(14):1690-1697.
Fojo et al., 1992, "Hypertriglyceridaemia due to genetic defects in lipoprotein lipase and apolipoprotein C-II," *J. of Int. Med.* 231:669-677.
Gregory et al., 2011, "Elongase Reactions as Control Points in Long-Chain Polyunsaturated Fatty Acid Synthesis," *PLoS One* 6(12) e29662:1-9.
Grimsgaard et al., 1997, "Highly purified eicosapentaenoic acid and docosahexaenoic acid in humans have similar triacylglycerol-lowering effects but divergent effects on serum fatty acids," *American Journal of Clinical Nutrition* 66:649-659.
Guil-Guerrero et al., 2001, "Purification Process for Cod Liver Oil Polyunsaturated Fatty Acids," *JAOCS* 78(5):477-484.
Hansen, et al., 1998, "Effects of Highly Purified Eicosapentaenoic Acid and Docosahexaenoic Acid on Fatty Acid Absorption, Incorporation into Serum Phospholipids and Postprandial Triglyceridemia," *Lipids* 33(2):131-138.
Harper et al., 2010, "Using Apolipoprotein B to Manage Dyslipidemic Patients: Time for a Change?," *Mayo Clin Proc* 85(5):440-445.
Harris et al., 1990, "Fish Oils in Hypertriglyceridemia: a dose-response study," *American Society for Clinical Nutrition* 51:399-406.
Harris et al., 1997, "Safety and Efficacy of Omacor in Severe Hypertriglyceridemia," *Journal of Cardiovascular Risk* 4:385-391.
Harris et al., 2007, "Comparison of the Effects of Fish and Fish-oil Capsules on the n-3 Fatty Acid content of Blood Cells and Plasma Phospholipids," *American Society for Nutrition* 86:1621-1625.
Harris et al., 2008, "Omega-3 fatty acids and coronary heart disease risk: clinical and mechanistic perspectives," *Atherosclerosis* 197(1):12-24.
Harris et al., 2008, "Role of Omega-3 Fatty Acids in Cardiovascular Disease Prevention," *Lipids Online Slide Library* 1-30.
Harris et al., 2009, "The Omega-3 Index: From Biomarker to Risk Marker to Risk Factor," *Current Atherosclerosis Report* 11:411-417.
Harris et al., 2010, "The Omega-3 Index: Clinical utility for therapeutic intervention," *Curr Cardiol Rep* 12:503-508.
Harris, W.S. et al., "RE: Plasma Phospholipid Fatty Acids and Prostate Cancer Risk in the Select Trial," JNCI Journal of the National Cancer Institute Advance Access published Mar. 31, 2014, p. 1 of 1.
Hawthorne et al., 1992, "Treatment of ulcerative colitis with fish oil supplementation: a prospective 12 month randomized controlled trial," *GUT* 33:922-928.
Hayes et al., 2001, "Triangular Phase Diagrams to Predict the Fractionation of Free Fatty Acid Mixtures Via Urea Complex Formation," *Separation Science and Technology* 36(1):45-58.
Hayes, 2005, "Purification of Free Fatty Acids via Urea Inclusion Compounds," *Handbook of Functional Lipids* 77-88.
Homma et al., 1991, "Effects of eicosapentaenoic acid on plasma lipoprotein subfractions and activities of lecithin: cholesterol acyltransferase and lipid transfer protein," *Atherosclerosis* 91(1):145-153.
Huang et al., 2012, "Effect of n-3 polyunsaturated fatty acid on gene expression of the critical enzymes involved in homocysteine metabolism," *Nutrition Journal* 11(6):1-8.
Kastelein et al., Abstract 16374: "Dose Response of a Novel Free-Fatty Acid Formulation of Omega-3 for the Management of Dyslipidemia in Patients with Severe Hypertriglyceridemia—EpanoVa for Lowering Very High TriglycErides (The EVOLVE Trial)," 2012 AHA Meeting.
Kastelein, J.J.P. et al., "Omega-3 free fatty acids for the treatment of severe hypertriglyceridemia: The EpanoVa fOr Lowering Very high TriglyceridEs (EVOLVE) trial," Journal of Clinical Lipidology (2014) 8, 94-106.
Kataoka,Y. et al., "Epanova and hypertriglyceridemia: pharmacological mechanisms and clinical efficacy," Future Cardiol. (2013) 9(2), 177-186.
Kaur et al., 2010, "Short-term docosapentaenoic acid (22:5n-3) supplementation increases tissue docosapentaenoic acid, DHA and EPA concentrations in rats," *British Journal of Nutrition* 103:32-37.
Kaur et al., 2011, "Docosapentaenoic acid (22:5n-3): A review of its biological effects," *Progress in Lipid Research* 50:28-34.
Kelley et al., 2007, "Docosahexaenoic Acid Supplementation Improves Fasting and Postprandial Lipid Profiles in Hypertriglyceridemic Men," *The American Journal of Clinical Nutrition* 86(2):324-333.
Kelley et al., 2009, "DHA supplementation decreases serum C-reactive protein and other markers of inflammation in hypertriglyceridemic men," *J. Nutrition* 139(3):495-501.
Kling et al., 2011, "Omega-3 Free Fatty Acids Demonstrate More Than 4-Fold Greater Bioavailability for EPA and DHA Compared

(56) References Cited

OTHER PUBLICATIONS with Omega-3-acid Ethyl Esters in Conjunction with a Low-Fat Diet: The Eclipse Study," *Encore presentation from XVII Drugs Affecting Lipid Metabolism Symposium* Mar. 2011.

Laidlaw et al., 2003, "Effects of Supplementation with Fish Oil-Derived n-3 Fatty Acids and Gamma-Linolenic Acid on Circulating Plasma Lipids and Fatty Acid Profiles in Women," *The American Journal of Clinical Nutrition* 77(1):37-42.

Lavie et al., 2009, "Omega-3 Polyunsaturated Fatty Acids and Cardiovascular Diseases," *Journal of the American college of Cardiology* 54(7):585-594.

Lawson et al., 1988, "Absorption of Eicosapentaenoic Acid and Docosahexaenoic Acid from Fish Oil Triacylglycerols or Fish Oil Ethyl Esters Co-Ingested with a High-Fat Meal," *Biochemical and Biophysical Research Communications* 156(2):960-963.

Lawson et al., 1988, "Human Absorption of Fish Oil Fatty Acids as Triacylglycerols, Free Acids, or Ethyl Esters," *Biochemical and Biophysical Research Communications* 156(1):328-335.

Lemaitre et al., 2011, "Genetic loci associated with plasma phospholipid n-3 fatty acids: A meta-analysis of genome-wide association studies from the CHARGE consortium," *PLoS Genetics* 7(7)e 1002193:1-12.

Liu et at., 2006, "Concentration of docosahexaenoic acid (DHA) and eicosapentaenoic acid (EPA) of tuna oil by urea complexation: optimization of process parameters," *Journal of Food Engineering* 73:203-209.

Maki et al., 2010, "Baseline lipoprotein lipids and low-density lipoprotein cholesterol response to prescription omega-3 acid ethyl ester added to Simvastatin therapy," *Am. J. Cardiol.* 105(10):1409-1412.

Maki et al., 2011, "Effects of Prescription Omega-3-Acid Ethyl Esters, Coadministered with Atorvastatin, on Circulating Levels of Lipoprotein Particles, Apolipoprotein CIII, and Lipoprotein-Associated Phospholipase A2 Mass in Men and Women with Mixed Dyslipidemia," *Journal of Clinical Lipidology* 5(6):483-492.

Maki, K.C. et al., "A Highly Bioavailable Omega-3 Free Fatty Acid Formulation Improves the Cardiovascular Risk Profile in High-Risk, Statin-Treated Patients With Residual Hypertriglyceridemia (the ESPIRIT Trial)," Clinical Therapeutics vol. 35, No. 9 1400-1411 (2013).

Matsuzaki, et al., 2009, "Incremental Effects of Eicosapentaenoic Acid on Cardiovascular Events in Statin-Treated Patients with Coronary Artery Disease," *Circulation Journal* 73:1283-1290.

Meyer et al., 2007, "Dose-Dependent Effects of Docosahexaenoic Acid Supplementation on Blood Lipids in Statin-Treated Hyperlipidaemic Subjects," *Lipids* 42:109-115.

Mori et al., 1999, "Docosahexaenoic Acid but not Eicosapentaenoic Acid Lowers Ambulatory Blood Pressure and Heart Rate in Humans," *Hypertension: Journal of the American Heart Association* 34:253-260.

Mori et al., 2000, "Purified eicosapentaenoic and docosahexaenoic acids have differential effects on serum lipids and lipoproteins, LDL particle size, glucose, and insulin in mildly hyperlipidemic men," *American Journal of Clinical Nutrition* 71:1085-1094.

Mori et al., 2006, "The independent effects of eicosapentaenoic acid and docosahexaenoic acid on cardiovascular risk factors in humans," *Curr Opin Clin Nutr Metab Care* 9:95-104.

Mori et al., 2011 "Eicosapentaenoic Acid and Docosahexaenoic Acid: Are They different?," *PUFA* 1-2.

Mozaffarian et al., 2012, "(n-3) Fatty Acids and Cardiovascular Health: Are Effects of EPA and DHA Shared or Complementary?," *American Society for Nutrition* (Suppl):614S-625S.

Nakamura et al., 2012, "Both EPA/AA ratio and absolute AA levels constitute an independent risk factor for coronary atherosclerosis in type 2 diabetic patients," *Endocrine Abstracts* 29 OC19.1.

Neubronner et al., 2011, "Enhanced Increase of Omega-3 Index in Response to Long-Term n-3 Fatty Acid Supplementation from Triacylglycerides Versus Ethyl Esters," European Journal of Clinical Nutrition 65:247-254.

Norris et al., 2012, "Omega-3 fatty acids cause dramatic changes in TLR4 and purinergic eicosanoid signaling," *Proceedings of the National Academy of Sciences of the United States of America* 109(22):8517-8522.

Notarnicola et al., 2011, "Polyunsaturated fatty acids reduce Fatty Acid Synthase and Hydroxy-Methyl-Glutaryl CoA-Reductase gene expression and promote apoptosis in HepG2 cell line," *Lipids in Health and Disease* 10(10)1-7.

Notarnicola et al., 2011, "Synergic effect of Eicosapentaenoic acid and Lovastatin on gene expression of HMGCoA ," *Lipids in Health and Disease* 10(10)1-7.

Nozue et al., 2013, "Effects of Serum n-3 to n-6 Polyunsaturated Fatty Acids Ratios on Coronary Atherosclerosis in Statin-Treated Patients With Coronary Artery Disease," *Am J Cardiol.* 111(1):6-11 (Epub Oct. 2, 2012).

Obajimi et al., 2005, "Differential Effects of Eicosapentaenoic and Docosahexaenoic Acids upon Oxidant-Stimulated Release and Uptake of Arachidonic Acid in Human Lymphoma U937 Cells," *Pharmacological Research* 52:183-191.

Offman, E. et al., "Steady-state bioavailablity of prescription omega-3 on a low-fat diet is significantly improved with a free fatty acid formulation compared with an ethyl ester formulation: the Eclipse II study," Vascular Health and Risk Management 2013:9 563-573.

Oliva et al., 2005, "Inherited Apolipoprotein A-V Deficiency in Severe Hypertriglyceridemia," *Arteriosclerosis, Thrombosis, and Vascular Biology* 25:411-417.

Omega-3-acid Ethyl Esters (European Pharmacopeia Sep. 20, 2001) 1668-1670.

Omthera Pharmaceuticals, Inc. & Rx Communications Group, LLC "Omthera Pharmaceuticals Presents Successful Phase 3 Results from EVOLVE and ESPRIT Clinical Studies for Epanova™; Both Trials Meet Primary and Secondary Endpoints," Press Release dated Nov. 5, 2012 1-4.

Omthera Pharmaceuticals, Inc. & Rx Communications Group, LLC, "Omthera Pharmaceuticals Announces Positive Long Term Bioavailability Data Comparing Epanova™ to Lovazak®", Press Release dated Jan. 9, 2012 1-2.

Omthera Pharmaceuticals, Inc. & Rx Communications Group, LLC, "Omthera Pharmaceuticals Announces Positive Top-Line from Phase 3 EVOLVE Study," Press Release dated Apr. 26, 2012 1-2.

Omthera Pharmaceuticals, Inc. & Rx Communications Group, LLC, "Omthera Pharmaceuticals Completes Enrollment of Pivotal Phase III EVOLVE Trial for Epanova™ in Patients with Very High Triglycerides," Press Release dated Nov. 29, 2011.

Omthera Pharmaceuticals, Inc. & Rx Communications Group, LLC, "Omthera Pharmaceuticals Initiates Pivotal Phase III EVOLVE Trial for Epanova™ in Patients with Very High Triglycerides," Press Release dated Mar. 14, 2011.

Omthera Pharmaceuticals, Inc. & Rx Communications Group, LLC, "Omthera Pharmaceuticals, Inc. Announces Initiation of the ECLIPSE Trial: Epanova Compared to Lovaza in a Pharmacokinetic Single-dose Evaluation," Press Release dated Nov. 8, 2010.

Omthera Pharmaceuticals, Inc. and Rx Communications Group, LLC, "Omthera Pharmaceuticals, Inc. Initiates Phase III ESPRIT Trial of Add-on Epanova™ to Statin Therapy in Patients with Hypertriglyceridemia," Press Release dated Aug. 15, 2011.

Omthera Pharmaceuticals, Inc., "Omthera Pharmaceuticals Developing the Best-In-Class Prescription Omega-3 Therapy", JP Morgan Healthcare Conference, San Francisco, CA dated Jan. 13, 2011.

Omthera Pharmaceuticals, Inc., "Omthera Pharmaceuticals Matching an Unmet Medical Need With a Best-In-Class Therapy," JP Morgan Healthcare Conference, San Francisco, CA, dated Jan. 20, 2012.

Otvos et al., 2011 "Clinical Implications of Discordance Between Low-Density Lipoprotein Cholesterol and Particle Number," Journal of Clinical Lipidology 5:105-113.

Ouguerram et al., 2006, "Effect of n-3 Fatty acids on Metabolism of apoB100-containing Lipoprotein in Type 2 Diabetic Subjects," *British Journal of Nutrition* 96:100-106.

PCT International Search Report from PCT/US13/20398 dated Mar. 13, 2013.

(56) References Cited

OTHER PUBLICATIONS

Pejic et al., 2006, "Hypertriglyceridemia," *The Journal of the American Board of Family Medicine* 19(3):310-316.

Phillipson et al., 1985, "Reduction of Plasma Lipids, Lipoproteins, and Apoproteins by Dietary Fish Oils in Patients with Hypertriglyceridemia," *The New England Journal of Medicine* 1210-1216.

Portolesi et al., 2007, "Competition between 24:5n-3 and ALA for Δ6 desaturase may limit the accumulation of DHA in HepG2 cell membranes," *Journal of Lipid Research* 48:1592-1598.

Rader et al., Abstract 19030: "Apolipoprotein C-III is Significantly Reduced by Prescription Omega-3 Free Fatty Acids (Epanova) in patients with Severe Hypertriglyceridemia and Changes Correlate with Increases in LDL-C: A Sub-analysis of the EVOLVE trial," 2012 AHA meeting.

Rupp et al., 2004, "Risk Stratification by the 'EPA+DHA Level' and the 'EPA/AA Ratio' Focus on Anti-Inflammatory and Antiarrhythmogenic Effects of Long-Chain Omega-3 Fatty Acids," *Herz* 29:673-685.

Saito et al., 2008, "Effects of EPA on Coronary Artery Disease in Hypercholesterolemic Patients with Multiple Risk Factors: Sub-Analysis of Primary Prevention Cases from the Japan EPA Lipid Intervention Study (JELIS)," *Atherosclerosis* 200:135-140.

Simopoulos, 2008, "The Importance of the Omega-6/Omega-3 Fatty Acid Ratio in Cardiovascular Disease and Other Chronic Diseases," *Experimental Biology and Medicine* 233:674-688.

Skulas-Ray et al., 2008, "Omega-3 fatty acid concentrates in the treatment of moderate hypertriglyceridemia," *Expert Opin. Pharmacother.* 9(7): 1237-48.

Sun et al., 2008, "Blood Concentrations of individual long-chain n-3 fatty acids and risk of nonfatal myocardial infarction," *American Society for Nutrition* 88:216-223.

Trehan, Naresh, 2006, "Cardiovascular Disease Trends in India," *Slide Presentation* 1-24.

Von Schacky C., 2011, "The Omega-3 Index as a risk factor for cardiovascular diseases," *Prostaglandins and other Lipid Mediators* 96(1-4):94-98.

Supplementary European Search Report and Opinion for European Application No. 13 78 7637 dated Nov. 16, 2015.

\* cited by examiner

US 9,492,545 B2

COMPOSITIONS OF STATINS AND OMEGA-3 FATTY ACIDS

1. CROSS-REFERENCE TO RELATED APPLICATIONS

This application claims the benefit under 35 U.S.C. §119 (e) of U.S. Provisional Application No. 61/643,764, filed May 7, 2012, the content of which is incorporated herein by reference in its entirety.

2. BACKGROUND

Pharmaceutical compositions rich in omega-3 polyunsaturated fatty acids (PUFAs) have been developed to treat a variety of clinical indications, including various disorders of blood lipids, including hypertriglyceridemia and mixed dyslipidemias. Statin monotherapy is widely used to treat hypercholesterolemia and other blood lipid disorders.

Numerous studies have reported on the increased benefits of combined treatment with statins and omega-3 PUFAs in various cardiovascular disorders (See Nakamura et al., 1999, *Int. J. Clin. Lab Res.* 29:22-25 and Davidson et al., 1997, *Am J Cardiol* 80:797-798). To improve patient convenience and compliance, dual compositions comprising statins and omega-3 PUFAs in esterified form have been described, but some statins are known to be poorly soluble in such formulations (see, e.g., U.S. Pat. No. 7,642,287), and no such dual composition is commercially available.

Therefore, there is a need in the art for compositions that combine statins and omega-3 PUFAs in a single oral unit dosage form, and that provide enhanced solubility and bioavailability. Such pharmaceutical compositions would improve patient convenience, and may allow for treatment with improved effectiveness, fewer excipients, and better patient compliance, than is provided by the administration of the two actives in separate unit dosage forms.

3. SUMMARY

The inventors have discovered that certain statins have unexpectedly greater solubility in a PUFA free acid solvent system, a PUFA composition in which each of the PUFA species is present substantially in the free acid form, as compared to their solubility in a PUFA ethyl ester solvent system, a PUFA composition in which each of the PUFA species is present substantially in esterified form. Accordingly, the present disclosure provides pharmaceutical compositions, oral unit dosage forms, dosage kits, and methods of treatment comprising at least one statin dissolved in a PUFA free acid solvent system. In typical embodiments, the statin is rosuvastatin. In some embodiments, the statin is atorvastatin, pravastatin, lovastatin, simvastatin, atorvastatin, fluvastatin, or pitavastatin.

In a first aspect, pharmaceutical compositions comprising at least one statin dissolved in a PUFA free acid solvent system are provided.

In various embodiments, at least 90% of the total polyunsaturated fatty acid in the PUFA free acid solvent system is present in the free acid form. In certain embodiments, at least 91%, at least 92%, at least 93%, at least 94%, at least 95%, at least 96%, at least 97%, at least 98%, even at least 99% of the total polyunsaturated fatty acid in the PUFA free acid solvent system is present in the free acid form.

In typical embodiments, the PUFA free acid solvent system comprises at least one, typically a plurality of, omega-3 PUFA species, wherein each of the omega-3 PUFA species is present substantially in the free acid form. In various embodiments, the composition comprises EPA, DHA, and DPA (n-3), each substantially in free acid form.

In some embodiments, at least 80% by weight of the statin is dissolved in the PUFA free acid solvent system (less than 20% by weight of the statin is undissolved in the solvent system), while in particular embodiments, at least 90% by weight of the statin is dissolved in the PUFA free acid solvent system (less than 10% by weight of the statin is undissolved in the solvent system).

In various embodiments, the one or more statins is dissolved in the PUFA free acid solvent system in an amount that permits administration of a therapeutic amount of statin in a convenient number of oral unit doses, which number of oral unit doses also suffices to deliver a therapeutic dose of omega-3 PUFAs.

In certain embodiments, the one or more statins is present in the pharmaceutical composition in an amount, per ml or per g of PUFA free acid solvent system, of at least about 5 mg, at least about 10 mg, at least about 15 mg, at least about 20 mg, at least about 25 mg, at least about 30 mg, at least about 40 mg, at least about 50 mg, at least about 60 mg, at least about 70 mg, at least about 80 mg, at least about 90 mg, even at least about 100 mg, at least about 110 mg, and in certain embodiment, at least about 120 mg.

In selected embodiments, one or more statins is present in the pharmaceutical composition in an amount, per ml or per g of PUFA free acid solvent system, of from about 2 mg to about 80 mg, from about 5 mg to about 60 mg, or from about 10 mg to about 40 mg, or from about 20 mg to about 30 mg. In various embodiments, the at least one statin is selected from the group consisting of rosuvastatin, pravastatin, lovastatin, simvastatin, atorvastatin, fluvastatin, and pitavastatin.

In another aspect, oral unit dosage forms comprising the pharmaceutical compositions of the disclosure are provided. In some embodiments, the pharmaceutical composition is encapsulated in a soft gelatin capsule. In various embodiments, the oral unit dosage form further comprises at least one coating on the exterior of the soft gelatin capsule. In some embodiments, each of the at least one coatings is selected from the group consisting of: cellulose acetate trimellitate, cellulose acetate phthalate and poly(ethylacrylate-methylacrylate).

In some embodiments, the soft gelatin capsule encapsulates 1-100 mg of a statin dissolved in about 250 mg, about 500 mg, or about 1000 mg of a PUFA free acid solvent system. In certain embodiments, the soft gelatin capsule encapsulates 2-40 mg of a statin dissolved in about 250 mg, about 500 mg, or about 1000 mg of a PUFA free acid solvent system.

In other aspects, the disclosure provides methods of treating a blood lipid disorder, comprising administering an effective amount of a pharmaceutical composition of the disclosure. The blood lipid disorder is selected, in certain embodiments, from the group consisting of: hypertriglyceridemia, hypercholesterolemia, coronary heart disease (CHD), hypertriglyceridemia, mixed dyslipidemias, heart failure, myocardial infarction, cardiac arrhythmias, ischemic dementia, hypertension, nephropathy, retinopathy, vascular disease, and atherosclerotic disease.

4. BRIEF DESCRIPTION OF THE FIGURES

Figure 2:
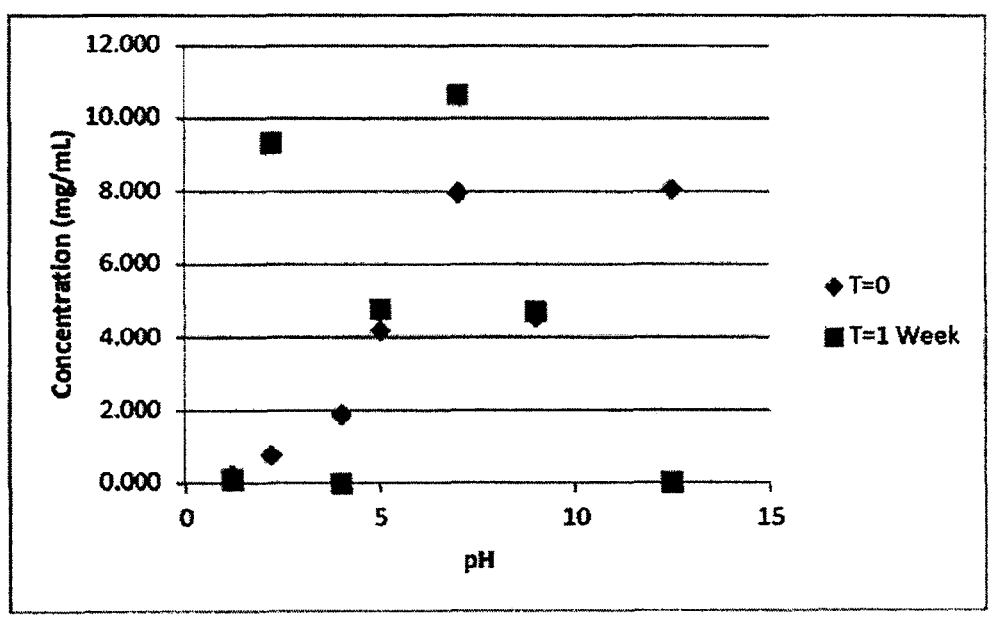

FIG. 1 provides data showing solubility of atorvastatin calcium in various pH buffers; and FIG. 2 provides data showing solubility of rosuvastatin calcium in various pH buffers.

5. DETAILED DESCRIPTION

5.1. Overview

Statins are known to be poorly soluble in compositions of omega-3 PUFAs in which the PUFAs are present substantially in esterified form ("PUFA ethyl ester solvent systems"). See, e.g., U.S. Pat. No. 7,642,287. The present inventors have now discovered that certain statins unexpectedly have significantly greater solubility in PUFA compositions in which each of the PUFA species is present substantially in the free acid form ("PUFA free acid solvent system"), as compared to their solubility in a PUFA ethyl ester solvent system. Accordingly, the present disclosure provides pharmaceutical compositions, oral unit dosage forms, and dosage kits comprising at least one statin dissolved in a PUFA free acid solvent system, and methods of using these compositions and unit oral dosage forms for treatment of blood lipid disorders. In typical embodiments, the statin is rosuvastatin. In some embodiments, the statin is atorvastatin, pravastatin, lovastatin, simvastatin, atorvastatin, fluvastatin, or pitavastatin.

5.2. Pharmaceutical Compositions

In a first aspect, pharmaceutical compositions comprising at least one statin dissolved in a PUFA free acid solvent system are provided. In typical embodiments, the PUFA free acid solvent system comprises at least one, typically a plurality of, omega-3 PUFA species, wherein each of the omega-3 PUFA species is present substantially in the free acid form. In some embodiments, the statin is rosuvastatin. In various embodiments, the statin is atorvastatin, pravastatin, lovastatin, simvastatin, atorvastatin, fluvastatin, or pitavastatin.

In some embodiments of the pharmaceutical composition, the statin is dissolved in the PUFA free acid solvent system to provide a substantially homogeneous composition.

In some embodiments, the statin is completely dissolved in the PUFA free acid solvent system. In various embodiments, the statin is substantially dissolved (i.e., at least about 90% of the statin is dissolved in the PUFA free acid solvent system, with about 10% or less of the statin is undissolved in the PUFA free acid solvent system). In certain embodiments, at least about 70% of the statin is dissolved in the PUFA free acid solvent system. In some embodiments, at least about 80%, 85%, 90%, 95%, even at least about 96%, 97%, 98%, 99%, even at least about 99.5% of the statin is dissolved in the PUFA free acid solvent system. In some embodiments, the statin is less than 30%, less than 20%, less than 15%, less than 10%, or less than 5% undissolved in the PUFA free acid solvent system.

In some embodiments, the pharmaceutical composition does not require significant amounts of compounds other than polyunsaturated fatty acids—such as surfactants, hydrophilic or hydrophobic solvents, oils or combinations thereof (individually and collectively, "non-PUFA solubilizers")—to dissolve the statin in the PUFA free acid solvent system.

Preferably, the statin is dissolved in the pharmaceutical composition without the use of any non-PUFA solubilizers.

If present, non-PUFA solubilizers are present in amounts of 50% or less (w/w) based on the total weight of the PUFA free acid solvent system, 40% or less, 30% or less, 20% or less, 10% or less, or 5% or less. In various embodiments, the weight ratio of polyunsaturated fatty acids to non-PUFA solubilizers is at least about 1:1, at least 5:1, or at least 10:1.

In some embodiments, the PUFA free acid solvent system contains no non-PUFA solubilizers.

Various embodiments of the pharmaceutical composition comprise a statin dissolved in a PUFA free acid solvent system, wherein the statin is present in the PUFA free acid solvent system in a weight-to-volume (w/v) ratio of about 1:5,000; about 1:4,500; about 1:4,000; about 1:3,50; about 1:3,000; about 1:2,500; about 1:2,000; about 1:1,500; about 1:1,000; about 1:800; about 1:700; about 1:500; about 1:400: about 1:300; about 1:250, about 1:125, about 1:100; about 1:80; about 1:50; or ratios intermediate the above-recited values.

In a variety of embodiments, at least one statin is dissolved in the PUFA free acid solvent system, wherein the statin is present in a weight-to-weight (w/w) ratio with respect to the PUFA free acid solvent system of about 1:5,000; about 1:4,500; about 1:4,000; about 1:3,500; about 1:3,000; about 1:2,500; about 1:2,000; about 1:1,500; about 1:1,000; about 1:800; about 1:700; about 1:500; about 1:400: about 1:300; about 1:250; about 1:125, about 1:100; about 1:80; about 1:50, or ratios intermediate these values.

In certain embodiments, the pharmaceutical composition comprises a statin dissolved in a PUFA free acid solvent system, wherein the statin is dissolved in the PUFA free acid solvent system at a concentration of at least about 0.1 mg/ml solvent system, 0.2 mg/ml, 0.5 mg/ml, 1 mg/ml, 2 mg/ml, 5 mg/ml, 7.5 mg/ml, 10 mg/ml, 15 mg/ml, 20 mg/ml, 30 mg/ml, 40 mg/ml, 50 mg/ml, 75 mg/ml, 100 mg/ml, 120 mg/ml, 150 mg/ml, or 200 mg/ml, or in concentrations intermediate these values. In various embodiments, the pharmaceutical composition comprises a statin dissolved in a PUFA free acid solvent system, wherein the statin is dissolved in the PUFA free acid solvent system at a concentration of at least about 0.1 mg/g solvent system, 0.2 mg/g solvent system, 0.5 mg/g solvent system, 1 mg/g solvent system, 2 mg/g solvent system, 5 mg/g solvent system, 7.5 mg/g solvent system, 10 mg/g solvent system, 15 mg/g solvent system, 20 mg/g solvent system, 30 mg/g solvent system, 40 mg/g solvent system, 50 mg/g solvent system, 75 mg/g solvent system, 100 mg/g solvent system, 120 mg/g solvent system, 150 mg/g solvent system, or 200 mg/g solvent system, or in concentrations intermediate these values.

5.2.1. PUFA Free Acid Solvent System

The PUFA free acid solvent system comprises at least one, typically a plurality of, species of omega-3 PUFAs, each present substantially in the free acid form.

In typical embodiments, the PUFA free acid solvent system comprises eicosapentaenoic acid (C20:5 n-3) ("EPA," also known as timnodonic acid) substantially in free acid form. In various embodiments, the PUFA free acid solvent system comprises docosahexaenoic acid (C22:6 n-3) ("DHA," also known as cervonic acid) substantially in free acid form. In selected embodiments, the PUFA free acid solvent system comprises docosapentaenoic acid (C22:5 n-3) ("DPA," also known as clupanodonic acid), substantially in free acid form.

In characteristic embodiments, the PUFA free acid solvent system comprises EPA, substantially in free acid form, in an amount, calculated as a percentage by area on GC chromatogram of all fatty acids in the PUFA free acid solvent system, of at least about 40% ("40% (a/a)"). In various embodiments, the PUFA free acid solvent system comprises EPA in an amount of at least about 41% (a/a), 42% (a/a), 43% (a/a), 44% (a/a), 45% (a/a), 46% (a/a), 47% (a/a), 48% (ala), 49% (a/a), or at least about 50% (a/a). In certain embodiments, the PUFA free acid solvent system comprises EPA, substantially in free acid form, in an amount of at least about 51% (a/a), at least about 52% (a/a), at least about 53% (a/a), at least about 54% (a/a), at least about 55% (a/a), at least about 56% (a/a), at least about 57% (a/a), at least about 58% (a/a), even at least about 59% (a/a), at least about 60% (a/a), at least about 61% (a/a), 62% (a/a), 63% (a/a), 64% (a/a), or 65% (a/a).

In a variety of embodiments, the PUFA free acid solvent system comprises EPA, substantially in free acid form, in an amount of at least about 70% (a/a), at least about 75% (a/a), at least about 80% (a/a), at least about 85% (a/a), 90% (a/a), 91% (a/a), 92% (a/a), 93% (a/a), 94% (a/a), even at least about 95% (a/a), 96% (a/a), 97% (a/a), 98% (a/a), or 99% (a/a).

In certain embodiments, the PUFA free acid solvent system comprises EPA, substantially in free acid form, in an amount of about 45 to about 65% (a/a). In particular embodiments, EPA is present, substantially in free acid form, in an amount of about 50 to about 60% (a/a). In various embodiments, EPA is present, substantially in free acid form, in an amount of about 52 to about 58.0% (a/a). In some embodiments, EPA is present, substantially in free acid form, in an amount of about 55% (a/a) to about 56% (a/a). In some embodiments, EPA is present in an amount of about 55% (a/a).

In various embodiments, the PUFA free acid solvent system comprises EPA, substantially in free acid form, in an amount, calculated as a percentage by mass of all fatty acids in the PUFA free acid solvent system ("% (m/m)"), of about 50% (m/m) to about 60% (m/m). In certain embodiments, EPA is present, substantially in free acid form, in an amount of about 55% (m/m).

In certain embodiments, the PUFA free acid solvent system comprises DHA, substantially in free acid form, in an amount of at least about 13% (a/a). In various embodiments, the PUFA free acid solvent system comprises DHA, substantially in free acid form, in an amount of at least about 14% (a/a), at least about 15% (a/a), at least about 16% (a/a), at least about 17% (a/a), at least about 18% (a/a), at least about 19% (a/a), or at least about 20% (a/a). In selected embodiments, the PUFA free acid solvent system comprises DHA, substantially in free acid form, in an amount of at least about 21% (a/a), at least about 22% (a/a), at least about 23% (ala), at least about 24% (a/a), even at least about 25% (a/a).

In a variety of embodiments, the PUFA free acid solvent system comprises DHA, substantially in free acid form, in an amount of at least about 30% (a/a), 35% (a/a), even at least about 40% (a/a).

In various embodiments, the PUFA free acid solvent system comprises DHA, substantially in free acid form, in an amount of about 13% (a/a) to about 25% (a/a). In certain embodiments, DHA is present, substantially in free acid form, in an amount of about 15% (a/a) to about 25% (a/a). In several embodiments, DHA is present, substantially in free acid form, in an amount of about 17% (a/a) to about 23% (a/a). In certain embodiments, DHA is present, substantially in free acid form, in an amount of about 19% (a/a) to about 20% (a/a).

In various embodiments, the PUFA free acid solvent systems comprise DHA, substantially in free acid form, in an amount of about 15% (m/m) to about 25% (m/m). In certain embodiments, DHA is present, substantially in free acid form, in an amount of about 17% (m/m) to about 23% (m/m). In certain embodiments, DHA is present, substantially in free acid form, in an amount of about 20% (m/m).

In certain embodiments, the PUFA free acid solvent system comprises DPA, substantially in free acid form, in an amount of at least about 1% (a/a). In various embodiments, the PUFA free acid solvent system comprises DPA, substantially in free acid form, in an amount of at least about 1.5% (a/a), 2% (a/a), 2.5% (a/a), 3% (a/a), 3.5% (a/a), 4% (a/a), 4.5% (a/a), even at least about 5% (a/a). In selected embodiments, the PUFA free acid solvent system comprises DPA, substantially in free acid form, in an amount of at least about 6% (a/a), at least about 7% (a/a), at least about 8% (a/a), or at least about 9% (a/a).

In a variety of embodiments, the PUFA free acid solvent system comprises DPA, substantially in free acid form, in an amount of about 1% (a/a) to about 8% (a/a). In certain embodiments, the PUFA free acid solvent system comprises DPA, substantially in free acid form, in an amount of about 2% (a/a) to about 7% (a/a). In selected embodiments, the PUFA free acid solvent system comprises DPA, substantially in free acid form, in an amount of about 3% (a/a) to about 6% (a/a). In particular embodiments, the PUFA free acid solvent system comprises DPA, substantially in free acid form, in an amount of about 4% (a/a) to about 5% (a/a).

In various embodiments, the PUFA free acid solvent system comprises DPA, substantially in free acid form, in an amount of no less than about 1% (m/m). In various embodiments, the PUFA free acid solvent system comprises DPA, substantially in free acid form, in an amount of about 1% (m/m) to about 8% (m/m). In particular embodiments, the PUFA free acid solvent system comprises DPA, substantially in free acid form, in an amount of no more than about 10% (m/m).

In a variety of embodiments, the PUFA free acid solvent system comprises EPA and DHA, each substantially in free acid form.

In various embodiments, the PUFA free acid solvent system comprises EPA and DHA, each substantially in free acid form, in a total amount of at least about 60% (a/a). In various embodiments, the PUFA free acid solvent system comprises EPA and DHA, each substantially in free acid form, in a total amount of at least about 61% (a/a), 62% (a/a), 63% (a/a), 64% (a/a), 65% (a/a), 66% (a/a), 67% (a/a), 68% (a/a), 69% (a/a), or at least about 70% (a/a). In particular embodiments, the PUFA free acid solvent system comprise EPA and DHA, each substantially in free acid form, in a total amount of at least about 71% (a/a), 72% (a/a), 73% (a/a), 74% (a/a), 75% (a/a), 76% (a/a), 77% (a/a), 78% (a/a), 79% (a/a), even at least about 80% (a/a). In certain embodiments, the PUFA free acid solvent system comprises EPA and DHA, each substantially in free acid form, in total amount of at least about 81% (a/a), 82% (a/a), at least about 83% (a/a), 84% (ala), even at least about 85% (a/a).

In various embodiments, the PUFA free acid solvent system comprises EPA and DHA, each substantially in free acid form, in a total amount of about 70% (m/m) to about 80% (m/m). In certain embodiments, the PUFA free acid solvent system comprises about 75% (m/m) EPA plus DHA, each substantially in free acid form.

In certain embodiments, the PUFA free acid solvent system comprises EPA and DHA, each substantially in free acid form, in mass ratios of at least about 2:1, 2.1:1, 2.2:1, 2.3:1, 2.4:1, 2.5:1, 2.6:1, 2.7:1, 2.8:1, 2.9:1, even at least about 3:1. In certain embodiments, the PUFA free acid solvent system comprises EPA and DHA, each substantially in free acid form, in a mass ratio of about 2.75:1.

In various embodiments, the PUFA free acid solvent system comprises EPA, DHA, and DPA, each substantially in free acid form, in a total amount of at least about 61% (a/a). In typical embodiments, the PUFA free acid solvent system comprises EPA, DHA, and DPA, each substantially in free acid form, in a total amount of at least about 62% (a/a), 63% (a/a), 64% (a/a), 65% (a/a), 66% (a/a), at least about 67% (a/a), at least about 68% (a/a), at least about 69% (a/a), or at least about 70% (a/a). In certain embodiments, the PUFA free acid solvent system comprises EPA, DHA, and DPA, each substantially in free acid form, in a total amount of at least about 71% (a/a), 72% (a/a), 73% (a/a), 74% (a/a), 75% (a/a), 76% (a/a), 77% (a/a), 78% (a/a), 79% (a/a), 80% (a/a), even at least about 81% (a/a), 82% (a/a), 83% (a/a), 84% (a/a), 85% (a/a), 86% (a/a), 87% (a/a), even at least about 88% (a/a).

In various embodiments, the PUFA free acid solvent system comprises EPA, DHA, and DPA, each substantially in free acid form, in a total amount of between about 70% (a/a) to about 90% (a/a).

In a particular series of embodiments, EPA, substantially in free acid form, is present in an amount of about 55% (a/a) to about 56% (a/a); DHA, substantially in free acid form, is present in an amount of about 19% (a/a) to about 20% (a/a); and DPA, substantially in free acid form, is present in an amount of about 4% (a/a) to about 5% (a/a). In certain embodiments, EPA, substantially in free acid form, is present in an amount of about 55% (m/m) to about 56% (m/m); DHA, substantially in free acid form, is present in an amount of about 19% (m/m) to about 20% (m/m); and DPA, substantially in free acid form, is present in an amount of about 4% (m/m) to about 5% (m/m).

In certain embodiments, the PUFA free acid solvent system is a complex mixture comprising a plurality of species of omega-3 PUFAs and a plurality of species of omega-6 PUFAs, each present substantially in free acid form.

In certain embodiments, the PUFA free acid solvent system comprises EPA, DHA, DPA, and further comprises one or more omega-3 polyunsaturated fatty acid species selected from the group consisting of α-linolenic acid (C18:3 n-3), moroctic acid (C18:4 n-3, also known as stearidonic acid), eicosatrienoic acid (C20:3 n-3), eicosatetraenoic acid (C20:4 n-3), and heneicosapentaenoic acid (C21:5 n-3), each substantially in the free acid form.

In particular embodiments, the PUFA free acid solvent system comprises EPA, DHA, DPA, and moroctic acid, each substantially in the free acid form. In a variety of embodiments, the PUFA free acid solvent system comprises EPA, DHA, DPA, moroctic acid, and heneicosapentaenoic acid, each substantially in the free acid form. In specific embodiments, the PUFA free acid solvent system comprises EPA, DHA, DPA, moroctic acid, heneicosapentaenoic acid, and eicosatetraenoic acid, each substantially in the free acid form. In selected embodiments, the PUFA free acid solvent system comprises EPA, DHA, DPA, α-linolenic acid (C18:3 n-3), moroctic acid (C18:4 n-3), eicosatrienoic acid (C20:3 n-3), eicosatetraenoic acid (C20:4 n-3), and heneicosapentaenoic acid (C21:5 n-3), each substantially in the free acid form.

In various embodiments, total omega-3 fatty acids—defined as the sum of alpha-linolenic acid (C18:3 n-3), moroctic acid (C18:4 n-3), eicosatrienoic acid (C20:3 n-3), eicosatetraenoic acid (C20:4 n-3), eicosapentaenoic acid (EPA) (C20:5 n-3), heneicosapentaenoic acid (C21:5 n-3), docosapentaenoic acid (C22:5 n-3) and docosahexaenoic acid (DHA) (C22:6 n-3), each present substantially in the free acid form—constitute from about 80% (a/a) to about 95% (a/a) of all fatty acids in the PUFA free acid solvent system. In a variety of embodiments, total omega-3 fatty acids constitute from about 80-about 95% (m/m) of all fatty acids in the PUFA free acid solvent system.

In various embodiments, the PUFA free acid solvent system further comprises one or more species of omega-6 PUFA, each present substantially in the free acid form.

In certain embodiments, the PUFA free acid solvent system comprises one or more species of omega-6 PUFA selected from the group consisting of linoleic acid (C18:2 n-6), gamma-linolenic acid (C18:3 n-6), eicosadienoic acid (C20:2 n-6), dihomo-gamma-linolenic acid (C20:3 n-6) ("DGLA"), arachidonic acid (C20:4 n-6) ("AA"), and docosapentaenoic acid (C22:5 n-6, also known as osbond acid).

In particular embodiments, the PUFA free acid solvent system comprises linoleic acid (C18:2 n-6), gamma-linolenic acid (C18:3 n-6), eicosadienoic acid (C20:2 n-6), dihomo-gamma-linolenic acid (C20:3 n-6) ("DGLA"), arachidonic acid (C20:4 n-6) ("AA"), and docosapentaenoic acid (C22:5 n-6), each present substantially in the free acid form.

In various embodiments, AA, substantially in free acid form, is present in an amount of no more than about 5% (a/a) of the fatty acids in the PUFA free acid solvent system. In certain embodiments, AA, substantially in free acid form, comprises no more than about 4.5% (a/a) of the fatty acids in the PUFA free acid solvent system. In particular embodiments, AA, substantially in free acid form, is present in an amount of no more than about 4% (a/a) of the fatty acids in the PUFA free acid solvent system.

In certain embodiments, AA, substantially in the form of the free acid, is present in an amount of no more than about 5% (m/m) of the fatty acids in the PUFA free acid solvent system. In certain embodiments, AA substantially in free acid form comprises no more than about 4.5% (m/m) of the fatty acids in the PUFA free acid solvent system. In particular embodiments, AA is present substantially in free acid form in an amount of no more than about 4% (m/m) of the fatty acids in the PUFA free acid solvent system.

In certain embodiments, total omega-6 polyunsaturated fatty acids—defined as the sum of linoleic acid (C18:2 n-6), gamma-linolenic acid (C18:3 n-6), eicosadienoic acid (C20:2 n-6), dihomo-gamma-linolenic acid (C20:3 n-6), arachidonic acid (C20:4 n-6) and docosapentaenoic acid (C22:5 n-6), each present substantially in the free acid form—comprise no more than about 10% (a/a) of the fatty acids in the PUFA free acid solvent system. In certain embodiments, total omega-6 polyunsaturated fatty acids comprise no more than about 10% (m/m) of the fatty acids in the PUFA free acid solvent system.

In specific embodiments, the PUFA free acid solvent system is given by Table 1, with each species of PUFA identified therein present substantially in free acid form and within the range of about −3 SD to about +3 SD of the respectively recited average. In certain embodiments, each species of PUFA identified therein is present substantially in free acid form and within the range of about −2 SD to about +2 SD of the respectively recited average. In certain embodiments, each species of PUFA identified therein is present substantially in free acid form and within the range of about −1 SD to about +1 SD of the respectively recited average. In selected embodiments, each species of PUFA identified therein is present substantially in free acid form and in an amount approximating the average amount respectively recited in Table 1.

In certain embodiments, the PUFA free acid solvent system is given by Table 2, with each species of PUFA identified therein present substantially in free acid form and within the range of about −3 SD to about +3 SD of the respectively recited average. In certain embodiments, each species is present substantially in free acid form and within the range of about −2 SD to about +2 SD of the respective average recited in Table 2. In certain embodiments, each PUFA species is present substantially in free acid form and within the range of about −1 SD to about +1 SD of the respectively recited average. In selected embodiments, each species of PUFA identified therein is present substantially in free acid form and in an amount approximating the average amount respectively recited in Table 2.

In certain embodiments, polyunsaturated fatty acids other than omega-3 and omega-6 polyunsaturated fatty acids are present in an amount of no more than about 5% (a/a). In various embodiments, polyunsaturated fatty acids other than omega-3 and omega-6 polyunsaturated fatty acids are present in an amount of no more than about 5% (m/m).

In a variety of embodiments, at least about 90% of each species of omega-3 PUFA present in the PUFA free acid solvent system is present in the free acid form. In certain embodiments, at least 91%, at least 92%, at least 93%, at least 94%, at least 95%, at least 96%, at least 97%, at least 98%, even at least 99% of each species of omega-3 PUFA present in the PUFA free acid solvent system is present in the free acid form. In exemplary embodiments, at least 90% of the total omega-3 polyunsaturated fatty acid content in the PUFA free acid solvent system is present in the free acid form. In certain embodiments, at least 91%, at least 92%, at least 93%, at least 94%, at least 95%, at least 96%, at least 97%, at least 98%, even at least 99% of the total omega-3 polyunsaturated fatty acid content in the PUFA free acid solvent system is present in the free acid form.

In various embodiments, at least 90% of each species of omega-6 PUFA present in the PUFA free acid solvent system is present in the free acid form. In certain embodiments, at least 91%, at least 92%, at least 93%, at least 94%, at least 95%, at least 96%, at least 97%, at least 98%, even at least 99% of each species of omega-6 PUFA in the PUFA free acid solvent system is present in the free acid form. In exemplary embodiments, at least 90% of the total omega-6 polyunsaturated fatty acid content in the PUFA free acid solvent system is present in the free acid form.

In various embodiments, at least 90% of the total polyunsaturated fatty acid content in the PUFA free acid solvent system is present in the free acid form. In certain embodiments, at least 91%, at least 92%, at least 93%, at least 94%, at least 95%, at least 96%, at least 97%, at least 98%, even at least 99% of the total polyunsaturated fatty acid in the PUFA free acid solvent system is present in the free acid form.

The PUFA free acid solvent system comprises, in typical embodiments, no more than about 3% (ala) saturated fatty acids and no more than about 5% (a/a) mono-unsaturated fatty acids. In various embodiments, the PUFA free acid solvent system comprises no more than about 3% (m/m) saturated fatty acids and no more than about 5% (m/m) mono-unsaturated fatty acids.

In typical embodiments, the PUFA free acid solvent system usefully further comprises an antioxidant. In certain embodiments, the antioxidant is butylated hydroxyanisole (BHA). In some embodiments, the antioxidant is alpha-tocopherol. In some embodiments, alpha-tocopherol is present in an amount of about 0.20-about 0.40% (m/m). In various embodiments, alpha-tocopherol is present in an amount of about 0.25-about 0.35% (m/m). In particular embodiments, alpha-tocopherol is present in an amount of about 0.27-about 0.33% (m/m). In typical embodiments, the PUFA free acid solvent system comprises no more than about 0.1 ppm ethyl carbamate. In some embodiments, the PUFA free acid solvent system comprises no more than 0.1 ppm ethyl carbamate. In various embodiments, the PUFA free acid solvent system comprises less than 0.1 ppm ethyl carbamate.

TABLE 1

PUFA free acid solvent system
10 batch statistics

| Identity | Common name | AVG | SD | −3SD | −2SD | −1SD | +1SD | +2SD | +3SD | 1SD Δ | 2SD Δ | 3SD Δ |
|---|---|---|---|---|---|---|---|---|---|---|---|---|
| C18:2(n-6) | Linoleic acid | 0.61 | 0.09 | 0.34 | 0.43 | 0.52 | 0.69 | 0.78 | 0.87 | 0.18 | 0.35 | 0.53 |
| C18:3(n-6) | Gamma-linolenic acid | 0.15 | 0.03 | 0.07 | 0.10 | 0.13 | 0.18 | 0.21 | 0.24 | 0.06 | 0.11 | 0.17 |
| C18:3(n-3) | α-Linolenic acid | 0.43 | 0.06 | 0.23 | 0.30 | 0.36 | 0.49 | 0.56 | 0.62 | 0.13 | 0.26 | 0.39 |
| C18:4(n-3) | Moroctic acid | 1.56 | 0.25 | 0.81 | 1.06 | 1.31 | 1.81 | 2.06 | 2.31 | 0.50 | 1.00 | 1.50 |
| C20:2(n-6) | Eicosadienoic acid | 0.13 | 0.05 | −0.03 | 0.02 | 0.07 | 0.18 | 0.23 | 0.29 | 0.11 | 0.21 | 0.32 |
| C20:3(n-6) | Dihomo-gamma-linolenic acid | 0.44 | 0.06 | 0.28 | 0.33 | 0.39 | 0.50 | 0.56 | 0.61 | 0.11 | 0.22 | 0.33 |
| C20:4(n-6) | Arachidonic acid | 3.14 | 0.58 | 1.41 | 1.99 | 2.57 | 3.72 | 4.29 | 4.87 | 1.15 | 2.30 | 3.46 |
| C20:3(n-3) | Eicosatrienoic acid | 0.20 | 0.04 | 0.08 | 0.12 | 0.16 | 0.24 | 0.28 | 0.32 | 0.08 | 0.16 | 0.24 |
| C20:4(n-3) | Eicosatetraenoic acid | 2.19 | 0.24 | 1.46 | 1.71 | 1.95 | 2.43 | 2.68 | 2.92 | 0.49 | 0.97 | 1.46 |
| C20:5(n-3) | Eicosapentaenoic acid (EPA) | 56.74 | 0.56 | 55.07 | 55.63 | 56.19 | 57.30 | 57.86 | 58.42 | 1.12 | 2.23 | 3.34 |
| C21:5(n-3) | Heneicosapentaenoic acid | 2.61 | 0.25 | 1.85 | 2.11 | 2.36 | 2.86 | 3.12 | 3.37 | 0.51 | 1.01 | 1.52 |
| C22:5(n-6) | Docosapentaenoic acid | 0.57 | 0.21 | −0.05 | 0.16 | 0.36 | 0.78 | 0.98 | 1.19 | 0.41 | 0.83 | 1.24 |
| C22:5(n-3) | Docosapentaenoic acid (DPA) | 5.31 | 1.06 | 2.13 | 3.19 | 4.25 | 6.37 | 7.42 | 8.48 | 2.12 | 4.23 | 6.35 |
| C22:6(n-3) | Docosahexaenoic acid (DHA) | 19.93 | 0.75 | 17.68 | 18.43 | 19.18 | 20.68 | 21.43 | 22.18 | 1.50 | 2.99 | 4.49 |

TABLE 2

PUFA free acid solvent system
21 batch statistics

| Identity | Common name | AVG % (a/a) | SD | −3SD | −2SD | −1SD | +1SD | +2SD | +3SD | 1SD Δ | 2SD Δ | 3SD Δ |
|---|---|---|---|---|---|---|---|---|---|---|---|---|
| C18:2(n-6) | Linoleic acid | 0.74 | 0.16 | 0.26 | 0.42 | 0.58 | 0.90 | 1.07 | 1.23 | 0.32 | 0.65 | 0.97 |
| C18:3(n-6) | Gamma-linolenic acid | 0.24 | 0.11 | −0.09 | 0.02 | 0.13 | 0.35 | 0.46 | 0.58 | 0.22 | 0.44 | 0.66 |
| C18:3(n-3) | α-Linolenic acid | 0.54 | 0.15 | 0.09 | 0.24 | 0.39 | 0.69 | 0.84 | 0.99 | 0.30 | 0.60 | 0.90 |
| C18:4(n-3) | Stearidonic (moroctic) acid | 2.83 | 1.49 | −1.63 | −0.15 | 1.34 | 4.31 | 5.80 | 7.28 | 2.97 | 5.94 | 8.92 |
| C20:2(n-6) | Eicosadienoic acid | 0.15 | 0.04 | 0.02 | 0.07 | 0.11 | 0.20 | 0.24 | 0.28 | 0.09 | 0.17 | 0.26 |
| C20:3(n-6) | Dihomo-gamma-linolenic acid | 0.40 | 0.07 | 0.18 | 0.25 | 0.32 | 0.47 | 0.55 | 0.62 | 0.15 | 0.30 | 0.45 |
| C20:4(n-6) | Arachidonic acid | 3.17 | 0.51 | 1.65 | 2.16 | 2.67 | 3.68 | 4.19 | 4.70 | 1.01 | 2.03 | 3.04 |
| C20:3(n-3) | Eicosatrienoic acid | 0.16 | 0.05 | 0.01 | 0.06 | 0.11 | 0.21 | 0.26 | 0.31 | 0.10 | 0.20 | 0.31 |
| C20:4(n-3) | Eicosatetraenoic acid | 2.13 | 0.41 | 0.92 | 1.32 | 1.73 | 2.54 | 2.94 | 3.35 | 0.81 | 1.62 | 2.43 |
| C20:5(n-3) | Timnodonic acid (EPA) | 55.40 | 2.13 | 49.00 | 51.13 | 53.27 | 57.53 | 59.66 | 61.80 | 4.26 | 8.53 | 12.79 |
| C21:5(n-3) | Heneicosapentaenoic acid | 2.33 | 0.34 | 1.29 | 1.64 | 1.98 | 2.67 | 3.02 | 3.36 | 0.69 | 1.38 | 2.07 |
| C22:5(n-6) | Docosapentaenoic acid | 0.58 | 0.16 | 0.11 | 0.27 | 0.43 | 0.74 | 0.90 | 1.06 | 0.31 | 0.63 | 0.94 |
| C22:5(n-3) | Docosapentaenoic acid (DPA) | 4.44 | 1.16 | 0.98 | 2.13 | 3.29 | 5.60 | 6.75 | 7.91 | 2.31 | 4.62 | 6.93 |
| C22:6(n-3) | Cervonic acid (DHA) | 19.35 | 1.69 | 14.28 | 15.97 | 17.66 | 21.04 | 22.73 | 24.42 | 3.38 | 6.76 | 10.14 |

5.2.2. Statins

In various embodiments, at least one statin is present in the pharmaceutical composition in an amount, per ml or per g of PUFA free acid solvent system, of at least about 2 mg, at least about 2.5 mg, at least about 5 mg, at least about 10 mg, at least about 15 mg, at least about 20 mg, at least about 25 mg, at least about 30 mg, at least about 40 mg, at least about 50 mg, at least about 60 mg, at least about 70 mg, at least about 80 mg, at least about 90 mg, even at least about 100 mg, at least about 110 mg, and in certain embodiment, at least about 120 mg.

In selected embodiments, at least one statin is present in the pharmaceutical composition in an amount, per ml or per g of PUFA free acid solvent system, of from about 2 mg to about 80 mg, from about 5 mg to about 60 mg, or from about 10 mg to about 40 mg, or from about 20 mg to about 30 mg.

In various embodiments, the at least one statin is selected from the group consisting of rosuvastatin, pravastatin, lovastatin, simvastatin, atorvastatin, fluvastatin, and pitavastatin.

In typical embodiments, the at least one statin is dissolved in the PUFA free acid solvent system in an amount that permits administration of a therapeutic amount of statin in a convenient number of oral unit doses, which number of oral unit doses also suffices to deliver a therapeutic dose of omega-3 PUFAs.

Rosuvastatin is marketed under the name Crestor® by Astra Zeneca, Wilmington, Del. In typical embodiments, rosuvastatin is dissolved in the PUFA free acid solvent system in an amount that permits daily administration, in a convenient number of oral doses, of 5 mg, 10 mg, 20 mg, 30 mg, 40 mg, 50 mg, 60 mg, 70 mg, 80 mg, even 90 mg or 100 mg. In particular embodiments, rosuvastatin is dissolved in the PUFA free acid solvent system in an amount, per ml or per g of PUFA solvent system, of 2.5 mg, 5 mg, 10 mg, 15 mg, 20 mg, 25 mg, 30 mg, 35 mg, 40 mg, even 45 mg or 50 mg. In certain embodiments, rosuvastatin is dissolved in the PUFA free acid solvent system in an amount, per ml or per g of PUFA solvent system, of 1.25 mg, 2.5 mg, 5 mg, 7.5 mg, 10 mg, 12.5 mg, 15 mg, 17.5 mg, 20 mg, 22.5 mg, even 25 mg.

Atorvastatin, which is marketed under the name Lipitor® by Pfizer, New York, N.Y., is hydrophobic and is known as a synthetic statin. In some embodiments, atorvastatin is dissolved in the PUFA free acid solvent system in an amount that permits daily administration, in a convenient number of oral doses, of from 2.5 to 100 mg, from 5 to 80 mg, and from 10 to 40 mg.

In particular embodiments, atorvastatin is dissolved in the PUFA free acid solvent system in an amount, per ml or per g of PUFA solvent system, of 2.5 mg, 5 mg, 10 mg, 15 mg, 20 mg, 25 mg, 30 mg, 35 mg, 40 mg, even 45 mg or 50 mg. In certain embodiments, atorvastatin is dissolved in the PUFA free acid solvent system in an amount, per ml or per g of PUFA solvent system, of 1.25 mg, 2.5 mg, 5 mg, 7.5 mg, 10 mg, 12.5 mg, 15 mg, 17.5 mg, 20 mg, 22.5 mg, even 25 mg.

Pravastatin, which is marketed as Pravachol® by Bristol-Myers Squibb, Princeton, N.J., is hydrophilic. Administered as monotherapy, pravastatin is best absorbed without food. In some embodiments, pravastatin is dissolved in the PUFA free acid solvent system in an amount that permits daily administration, in a convenient number of oral doses, of from 2.5 to 80 mg, from 5 to 60 mg, or from 10 to 40 mg.

In particular embodiments, pravastatin is dissolved in the PUFA free acid solvent system in an amount, per ml or per g of PUFA solvent system, of 2.5 mg, 5 mg, 10 mg, 15 mg, 20 mg, 25 mg, 30 mg, 35 mg, 40 mg, even 45 mg or 50 mg. In certain embodiments, pravastatin is dissolved in the PUFA free acid solvent system in an amount, per ml or per g of PUFA solvent system, of 1.25 mg, 2.5 mg, 5 mg, 7.5 mg, 10 mg, 12.5 mg, 15 mg, 17.5 mg, 20 mg, 22.5 mg, even 25 mg.

Lovastatin, which is marketed under the name Mevacor® by Merck, Whitehouse Station, N.J., is hydrophobic. In some embodiments, lovastatin is dissolved in the PUFA free acid solvent system in an amount that permits daily administration, in a convenient number of oral doses, of from 2.5 to 100 mg, from 5 to 80 mg, or from 10 to 40 mg.

In particular embodiments, lovastatin is dissolved in the PUFA free acid solvent system in an amount, per ml or per g of PUFA solvent system, of 2.5 mg, 5 mg, 10 mg, 15 mg, 20 mg, 25 mg, 30 mg, 35 mg, 40 mg, even 45 mg or 50 mg. In certain embodiments, lovastatin is dissolved in the PUFA free acid solvent system in an amount, per ml or per g of PUFA solvent system, of 1.25 mg, 2.5 mg, 5 mg, 7.5 mg, 10 mg, 12.5 mg, 15 mg, 17.5 mg, 20 mg, 22.5 mg, even 25 mg.

Simvastatin, which is marketed under the name Zocor® by Merck, Whitehouse Station, N.J., is hydrophobic. In some embodiments, simvastatin is dissolved in the PUFA free acid solvent system in an amount that permits daily administration, in a convenient number of oral doses, of from 1 to 80 mg per day, from 2 to 60 mg, or from 5 to 40 mg per day.

In particular embodiments, simvastatin is dissolved in the PUFA free acid solvent system in an amount, per ml or per g of PUFA solvent system, of 2.5 mg, 5 mg, 10 mg, 15 mg, 20 mg, 25 mg, 30 mg, 35 mg, 40 mg, even 45 mg or 50 mg. In certain embodiments, simvastatin is dissolved in the PUFA free acid solvent system in an amount, per ml or per g of PUFA solvent system, of 1.25 mg, 2.5 mg, 5 mg, 7.5 mg, 10 mg, 12.5 mg, 15 mg, 17.5 mg, 20 mg, 22.5 mg, even 25 mg.

Fluvastatin, which is marketed under the name Lescol® by Novartis, East Hanover, N.J., is hydrophilic and is known as a synthetic statin. In various embodiments, fluvastatin is dissolved in the PUFA free acid solvent system in an amount that permits daily administration, in a convenient number of oral doses, of from 5 to 160 mg, from 10 to 120 mg, and from 20 to 80 mg.

In particular embodiments, fluvastatin is dissolved in the PUFA free acid solvent system in an amount, per ml or per g of PUFA solvent system, of 2.5 mg, 5 mg, 10 mg, 15 mg, 20 mg, 25 mg, 30 mg, 35 mg, 40 mg, even 45 mg or 50 mg. In certain embodiments, fluvastatin is dissolved in the PUFA free acid solvent system in an amount, per ml or per g of PUFA solvent system, of 1.25 mg, 2.5 mg, 5 mg, 7.5 mg, 10 mg, 12.5 mg, 15 mg, 17.5 mg, 20 mg, 22.5 mg, even 25 mg.

Pitavastatin is marketed under the name Livalo® by Kowa Pharmaceuticals America, Inc., Montgomery, Ala. and Lilly USA, Indianapolis, Ind. The dosage of pitavastatin in the pharmaceutical composition can be from 2.5 to 80 mg, from 2.5 to 60 mg, or from 5 to 40 mg.

In particular embodiments, pitavastatin is dissolved in the PUFA free acid solvent system in an amount, per ml or per g of PUFA solvent system, of 2.5 mg, 5 mg, 10 mg, 15 mg, 20 mg, 25 mg, 30 mg, 35 mg, 40 mg, even 45 mg or 50 mg. In certain embodiments, pitavastatin is dissolved in the PUFA free acid solvent system in an amount, per ml or per g of PUFA solvent system, of 1.25 mg, 2.5 mg, 5 mg, 7.5 mg, 10 mg, 12.5 mg, 15 mg, 17.5 mg, 20 mg, 22.5 mg, even 25 mg.

In typical embodiments, the pharmaceutical composition comprises a statin which is more soluble in a PUFA free acid solvent system than in a PUFA ethyl ester solvent system. In some embodiments, the pharmaceutical composition comprises a hydrophobic statin which is more soluble in a PUFA free acid solvent system than in a PUFA ethyl ester solvent system. In some embodiments, the pharmaceutical composition comprises a hydrophobic statin which is more soluble in a PUFA free acid solvent system than in a PUFA ethyl ester solvent system.

5.3. Oral Unit Dosage Forms

In another aspect, the pharmaceutical composition is usefully packaged in unit dosage forms for oral administration.

In particular embodiments, the dosage form is a capsule. In certain embodiments, the dosage form is a hard gelatin capsule. In other embodiments, the dosage form is a soft gelatin capsule.

In various embodiments, the capsule comprises Type A gelatin. In certain embodiments, the capsule comprises Type B gelatin. In some embodiments, the capsule comprises both Type A and Type B gelatin. Sources of collagen for the production of either type A or type B gelatin include, but are not limited to, cows, pigs and fish.

In various embodiments, the capsule is a soft gelatin capsule in which at least about 1% (w/w) of the gelatin is Type A gelatin. In certain embodiments, at least about 2% (w/w), 3% (w/w), 4%, (w/w), 5% (w/w), 6% (w/w), 7% (w/w), 8% (w/w), 9% (w/w), or at least about 10% (w/w) of the gelatin is Type A gelatin. In selected embodiments, at least about 15% (w/w), 20% (w/w), 25% (w/w), 30% (w/w), 35% (w/w), 40% (w/w), 45% (w/w), even at least about 50% (w/w), 55% (w/w), 60% (w/w), 65% (w/w), 70% (w/w), 75% (w/w), 80% (w/w), 85% (w/w), 90% (w/w), 95% or more of the gelatin is Type A gelatin.

In particular embodiments, the gelatin of the capsule consists essentially of type A gelatin.

In a selection of embodiments, sufficient Type A gelatin is present such that the capsule, when lacking an exterior coating such as those described below, disintegrates within a time period of not more than 30 minutes in purified water at 37° C. after storage for at least 3 months at 40° C. In certain embodiments, the capsule is a soft gelatin capsule comprising sufficient Type A gelatin such that the capsule, uncoated, disintegrates within a time period of not more than 30 minutes in purified water at 37° C. after storage for at least 6 months at 40° C.

In various embodiments, the capsule is a soft gelatin capsule comprising sufficient Type A gelatin such that the capsule, when uncoated, disintegrates within a time period of not more than 30 minutes in purified water at 37° C. after storage for at least 3 months at 30° C. In certain embodiments, the capsule is a soft gelatin capsule comprising sufficient Type A gelatin such that the capsule, when not coated, disintegrates within a time period of not more than 30 minutes in purified water at 37° C. after storage for at least 6 months at 30° C. In some embodiments, the capsule is a soft gelatin capsule comprising sufficient Type A gelatin such that the capsule in an uncoated state disintegrates within a time period of not more than 30 minutes in purified water at 37° C. after storage for at least 9 months at 30° C. In some embodiments, the capsule is a soft gelatin capsule comprising sufficient Type A gelatin such that the capsule, if not further coated, disintegrates within a time period of not more than 30 minutes in purified water at 37° C. after storage for at least 12 months at 30° C.

In certain embodiments, the Type A gelatin is porcine Type A gelatin.

In some embodiments, the capsule is a reduced cross-linked gelatin capsule, such as those described in U.S. Pat. No. 7,485,323, incorporated herein by reference in its entirety. In a variety of embodiments, capsules are made from substances that are not animal by-products, such as alginate, agar-agar, carrageenan, pectin, konjak, guar gum, food starch, modified corn starch, potato starch, and tapioca. Non-animal sources of materials that can be used to make capsules are described in U.S. Patent Publication No. 2011/0117180, incorporated herein by reference. In some embodiments, Vegicaps Capsules (Catalent) are used.

In certain embodiments, the capsule comprises a chemically-modified gelatin. In various embodiments, the chemically-modified gelatin is a succinylated gelatin.

In certain capsular oral unit dosage form embodiments, the capsule is uncoated. In a variety of embodiments, the capsule is coated.

In certain coated capsule embodiments, the capsule is coated with a coating on the exterior of the capsule that causes the encapsulated pharmaceutical composition to be released in a time-dependent manner. In various embodiments, release of the pharmaceutical composition is delayed for at least 15 minutes after ingestion. In particular embodiments, release of the pharmaceutical composition is delayed for at least 30 minutes after ingestion. In other embodiments, release of the fatty acid composition is delayed for about 30 minutes-about 60 minutes after ingestion. In various coated embodiments, the coating is selected from cellulose acetate trimellitate, cellulose acetate phthalate and poly(ethylacrylate-methylacrylate). In some embodiments, the coating is a neutral polyacrylate such as poly(ethylacrylatemethylmethacrylate), such as Eudragit NE 30-D (Evonik Industries AG), which has an average molecular weight of about 800,000.

In certain embodiments, capsules are coated as described in U.S. Pat. Nos. 5,792,795 and 5,948,818, the disclosures of which are incorporated herein by reference. In certain embodiments, the dosage form is a coated soft gelatin capsule comprising porcine type A gelatin, as described in U.S. Pat. No. 7,960,370, incorporated herein by reference.

In various embodiments, the oral unit dosage form contains from about 100 mg to about 2000 mg of the pharmaceutical composition described herein. In some embodiments, the oral dosage form contains about 250 mg of the pharmaceutical composition. In some embodiments, the oral dosage form contains about 500 mg of the pharmaceutical composition. In certain embodiments, the oral dosage form contains about 750 mg of the pharmaceutical composition. In some embodiments, the oral dosage form contains about 1000 mg of the pharmaceutical composition. In other embodiments, the oral dosage form contains about 1500 mg of the pharmaceutical composition. In certain embodiments, the unit dosage form contains nonintegral weight amounts of pharmaceutical composition, typically between 100 mg and 2000 mg.

In some embodiments, the dosage form encapsulates PUFAs in an amount of about 50 mg to about 5000 mg, about 75 mg to about 2500 mg, or about 100 mg to about 1000 mg, for example about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050 mg, about 1075 mg, about 1100 mg, about 1025 mg, about 1050 mg, about 1075 mg, about 1200 mg, about 1225 mg, about 1250 mg, about 1275 mg, about 1300 mg, about 1325 mg, about 1350 mg, about 1375 mg, about 1400 mg, about 1425 mg, about 1450 mg, about 1475 mg, about 1500 mg, about 1525 mg, about 1550 mg, about 1575 mg, about 1600 mg, about 1625 mg, about 1650 mg, about 1675 mg, about 1700 mg, about 1725 mg, about 1750 mg, about 1775 mg, about 1800 mg, about 1825 mg, about 1850 mg, about 1875 mg, about 1900 mg, about 1925 mg, about 1950 mg, about 1975 mg, about 2000 mg, about 2025 mg, about 2050 mg, about 2075 mg, about 2100 mg, about 2125 mg, about 2150 mg, about 2175 mg, about 2200 mg, about 2225 mg, about 2250 mg, about 2275 mg, about 2300 mg, about 2325 mg, about 2350 mg, about 2375 mg, about 2400 mg, about 2425 mg, about 2450 mg, about 2475 mg or about 2500 mg.

In various embodiments, the pharmaceutical composition present in the unit dosage form is stable at room temperature (about 23° C. to 27° C., or about 25° C.) and about 60% relative humidity for a period of at least six months, at least one year, or at least two years. By "stable" is intended that the solubilized statin does not precipitate out of solution to any appreciable degree, for example, in amounts of less than 10%, preferably less than 5%, of the originally dissolved statin.

5.4. Dosage Kits

In another aspect, a plurality of unit dosage forms as above-described may usefully be packaged together in a dosage kit to increase ease of use and patient compliance.

In certain embodiments, the dosage kit is a bottle. In other embodiments, the plurality of dosage forms is packaged in blister packs, a plurality of which blister packs may optionally be packaged together in a box or other enclosure. Typically, whether in a bottle or one or more blister packs, the plurality of unit dosage forms is sufficient for 30 days, 60 days, or 90 days of dosing. Thus, in selected embodiments, in which the unit dosage form is a capsule that encapsulates approximately one gram of the pharmaceutical composition as described herein above, the dosage kit comprises 30, 60, 90, 120, 150, 180, 240, 270, or 300 such capsules.

In various embodiments, the plurality of unit dosage forms is packaged under an inert gas, such as nitrogen or a noble gas, or is packaged under vacuum.

5.5. Dosing and Administration

In typical embodiments, the pharmaceutical composition is administered from 1 to 4 times a day, e.g. twice a day, with each dose comprising from 1 to 10 unit doses, such as capsules, as described herein. In typical embodiments, the administration is oral administration, although other routes of administration may be used.

In certain embodiments, at least about 2 g of the pharmaceutical composition is administered per day. In some embodiments, at least about 3 g of the pharmaceutical composition is administered per day. In certain embodiments, at least about 4 g of the pharmaceutical composition is administered per day. Typically, the pharmaceutical is administered as a plurality of unit dosage forms, such as those described above. Thus, in certain embodiments, at least 2 unit dosage forms, each comprising 1 g of the pharmaceutical composition, are administered per day. In various embodiments, at least 3 unit dosage forms, each comprising 1 g of the pharmaceutical composition, are administered per day. In particular embodiments, at least 4 unit dosage forms, each comprising 1 g of the pharmaceutical composition, are administered per day.

5.6. Methods of Treatment

In another aspect, methods of treating a blood lipid disorder are presented, comprising administering a pharmaceutical composition or compositions as described herein, typically in the form of unit dosage forms as described herein, in an amount and for a duration sufficient to treat the blood lipid disorder. Blood lipid disorders include, but are not limited to hypertriglyceridemia, dyslipidemias, hypercholesterolemia, coronary heart disease (CHD), heart failure, myocardial infarction, cardiac arrhythmias, ischemic dementia, hypertension, coagulation related disorders, nephropathy, retinopathy, vascular disease, atherosclerotic disease and related conditions. Methods of the disclosure are also directed to the treatment and/or prevention and/or reduction of cardiac events, cardiovascular events and symptoms.

The present combination of a statin and omega-3 fatty acids in a single composition may allow for a greater effect than any expected combined or additive effect of the two drugs alone. Moreover, the combined or additive effect of the two drugs may depend on the initial level of lipid parameter in the blood of a subject.

In some embodiments, upon treatment in accordance with the present invention, the subject exhibits an improvement in one or more parameters associated with a blood lipid disorder. Non-limiting examples of such improved parameters are reduced triglyceride levels compared to baseline or placebo control; reduced Apo B levels compared to baseline or placebo control; reduced Apo CIII levels compared to baseline or placebo control; increased HDL-C levels compared to baseline or placebo control; a reduction in LDL-C levels compared to baseline or placebo control; a reduction in non-HDL-C levels compared to baseline or placebo control; a reduction in vLDL levels compared to baseline or placebo control; an increase in Apo A-I levels compared to baseline or placebo control; an increase in Apo A-I/Apo B ratio compared to baseline or placebo control; a reduction in lipoprotein a levels compared to baseline or placebo control; a reduction in LDL particle number compared to baseline or placebo control; a reduction in LDL particle size compared to baseline or placebo control; a reduction in remnant-like particle cholesterol compared to baseline or placebo control; a reduction in oxidized LDL compared to baseline or placebo control; a reduction in fasting plasma glucose (FPG) compared to baseline or placebo control; a reduction in hemoglobin A (HbA) compared to baseline or placebo control; a reduction in homeostasis model insulin resistance compared to baseline or placebo control; a reduction in lipoprotein associated phospholipase A2 compared to baseline or placebo control; a reduction in intracellular adhesion molecule-1 compared to baseline or placebo control; a reduction in interleukin-2 compared to baseline or placebo control; a reduction in plasminogen activator inhibitor-1 compared to baseline or placebo control; a reduction in high sensitivity C-reactive protein (hsCRP) compared to baseline or placebo control; an increase in serum phospholipid EPA compared to baseline or placebo control; an increase in red blood cell membrane EPA compared to baseline or placebo control; a reduction in serum or plasma arachidonic acid (AA) level compared to baseline or placebo control; an increase in plasma or red blood cell membrane EPA/arachidonic acid (AA) ratio; and an increase in omega-3:omega-6 ratio.

Measurements of parameters associated with a blood lipid disorder can be made using methods known in the art. Measurements can be made to determine baseline levels of one or more parameters associated with a blood lipid disorder, prior to treatment, or during the course of treatment.

For example, triglycerides, total cholesterol, HDL-C and fasting blood sugar can be sampled from serum or plasma and analyzed using standard photometry techniques. VLDL-TG, LDL-C and VLDL-C can be calculated or determined using serum lipoprotein fractionation by preparative ultracentrifugation and subsequent quantitative analysis by refractometry or by analytic ultracentrifugal methodology. Apo A1, Apo B and hsCRP can be determined from serum using standard nephelometry techniques. Lipoprotein (a) can be determined from serum using standard turbidimetric immunoassay techniques. LDL particle number and particle size can be determined using nuclear magnetic resonance (NMR) spectrometry. Remnants lipoproteins and LDL-phospholipase A2 can be determined from EDTA plasma or serum and serum, respectively, using enzymatic immunoseparation techniques. Oxidized LDL, intercellular adhesion molecule-1 and interleukin-2 levels can be determined from serum using standard enzyme immunoassay techniques. These techniques are described in detail in standard textbooks, for example Tietz Fundamentals of Clinical Chemistry, 6th Ed. (Burtis, Ashwood and Borter Eds.), WB Saunders Company.

In some embodiments, a subject fasts for up to 12 hours prior to blood sample collection, for example about 10 hours.

5.6.1. Treatment of Severe Hypertriglyceridemia (≥500 mg/dL)

In various embodiments, the method is a method of treating severe (≥500 mg/dL) hypertriglyceridemia, the method comprising orally administering the pharmaceutical composition described herein to a patient having pre-treatment serum or plasma triglyceride levels ≥500 mg/dL, in an amount and for a duration effective to reduce serum or plasma triglycerides below pre-treatment levels.

In certain embodiments, the method comprises administering the pharmaceutical composition in an amount and for a duration effective to reduce serum or plasma triglyceride levels by at least about 5%, 6%, 7%, 8%, or at least about 9% below pre-treatment levels. In certain embodiments, the composition is administered in an amount and for a duration effective to reduce serum or plasma triglyceride levels by at least 10%, 11%, 12%, 13%, 14%, 15%, 16%, 17%, 18% or 19% below pre-treatment levels. In particular embodiments, the composition is administered in an amount and for a duration effective to reduce serum or plasma triglyceride levels by at least about 20% below pre-treatment levels. In various embodiments, the pharmaceutical composition is administered in an amount and for a duration effective to reduce serum or plasma triglycerides by at least about 25%, 30%, 35%, 40%, 45%, even at least about 50% below pre-treatment levels.

In a series of embodiments, the pharmaceutical composition is administered in an amount and for a duration effective to reduce serum or plasma triglyceride levels by at least about 50 mg/dL, 60 mg/dL, 70 mg/dL, 80 mg/dL, 90 mg/dL, even at least about 100 mg/dL. In certain embodiments, the composition is administered in an amount and for a duration effective to reduce serum or plasma triglyceride levels by at least about 110 mg/dL, 120 mg/dL, 130 mg/dL, 140 mg/dL, even at least about 150 mg/dL. In specific embodiments, the pharmaceutical composition is administered in an amount and for a duration effective to reduce serum or plasma triglyceride levels by at least about 160 mg/dL, 170 mg/dL, 180 mg/dL, even at least about 190 mg/dL or 200 mg/dL.

In some embodiments, the pharmaceutical composition described herein is administered in an amount and for a duration sufficient to reduce non-HDL-cholesterol by at least about 1%, at least about 2%, at least about 3%, 4%, 5%, even at least about 7%, 8%, 9%, or at least about 10% below pre-treatment levels. In certain embodiments, the pharmaceutical composition is administered in an amount and for a duration sufficient to reduce non-HDL-cholesterol by at least about 15%, at least about 20%, at least about 25%, at least about 30%, at least about 35%, at least about 40% below pre-treatment levels.

In various embodiments, the pharmaceutical composition is administered in an amount and for a duration effective to increase HDL-c levels by at least about 1% above pre-treatment levels. In certain embodiments, the pharmaceutical composition is administered in an amount and for a duration sufficient to increase HDL-c by at least about 2%, 3%, 4%, even at least about 5%, 6%, 7%, 8%, 9%, or 10% above pre-treatment levels.

In certain embodiments, the pharmaceutical composition is administered in an amount and for a duration effective to reduce the total cholesterol:HDL-c ("TC/HDL") ratio by at least about 1% below pre-treatment levels. In some embodiments, the pharmaceutical composition is administered in an amount and for a duration sufficient to reduce the TC/HDL ratio by at least about 2%, 3%, 4%, 5%, 6%, 7%, 8%, even at least about 9% or at least about 10% below pre-treatment levels.

In some embodiments, the pharmaceutical composition is administered in an amount and for a duration effective to decrease VLDL-c levels by at least about 5%, 6%, 7%, 8%, 9%, or at least about 10% below pre-treatment levels. In certain embodiments, the pharmaceutical composition is administered in an amount and for a duration sufficient to decrease VLDL-c levels by at least about 11%, 12%, 13%, 14%, 15%, 16%, 17%, even at least about 18%, 19%, or 20% below pre-treatment levels. In particular embodiments, the pharmaceutical composition is administered in an amount and for a duration sufficient to decrease VLDL-c levels by at least about 21%, 22%, 23%, 24%, even at least about 25% below pre-treatment levels.

In a variety of embodiments, the pharmaceutical composition is administered in an amount and for a duration effective to decrease ApoCIII levels. In certain embodiments, the pharmaceutical composition is administered in an amount and for a duration sufficient to decrease ApoCIII levels by at least about 1%, 2%, 3%, 4%, 5%, 6%, 7%, even at least about 8%, 9% or 10% below pre-treatment levels.

In some embodiments, the pharmaceutical composition is administered in an amount and for a duration effective to increase plasma EPA levels by at least about 100% above pre-treatment levels. In certain embodiments, the pharmaceutical composition is administered in an amount and for a duration effective to increase plasma EPA levels by at least about 200%, 250%, 300%, even at least about 350%, 400%, 450% or at least about 500% above pre-treatment levels. In selected embodiments, the pharmaceutical composition is administered for a time and in an amount effective to increase plasma EPA levels by at least about 550%, 600%, 650%, even at least about 700% above pre-treatment levels.

In various embodiments, the pharmaceutical composition is administered in an amount and for a duration effective to increase plasma DHA levels by at least about 50% above pre-treatment levels. In particular embodiments, the pharmaceutical composition is administered in an amount and for a duration effective to increase plasma DHA levels by at least about 55%, 60%, 65%, 70%, even at least about 75%, 80%, 85%, or 90% above pre-treatment levels.

In a series of embodiments, the pharmaceutical composition is administered in an amount and for a duration effective to increase plasma DPA levels by at least about 50% above pre-treatment levels. In some embodiments, the pharmaceutical composition is administered in an amount and for a duration effective to increase plasma DPA levels by at least about 55%, 60%, 65%, 70%, 75%, even at least about 80%, 85%, 90%, 95%, or 100% above pre-treatment levels. In selected embodiments, the pharmaceutical composition is administered in an amount and for a duration effective to increase plasma DPA levels by at least about 110%, 120%, even at least about 125% above pre-treatment levels.

In a series of embodiments, the pharmaceutical composition is administered in an amount and for a duration effective to reduce arachidonic acid (AA) concentration in plasma by at least about 5% below pre-treatment levels. In certain embodiments, the pharmaceutical composition is administered in an amount and for a duration effective to reduce arachidonic (AA) concentration in plasma by at least about 6%, 7%, 8%, 9%, 10%, even at least about 11%, 12%, 13%, 14%, even at least about 15%, 16%, 17%, 18%, 19%, 20%, or 21%, 22%, 23%, 24% even at least about 25% below pre-treatment levels.

In certain embodiments, the pharmaceutical composition is administered in an amount, and for a duration, effect to reduce plasma arachidonic acid concentration by at least about 25 µg/mL. In some embodiments, the pharmaceutical composition is administered in an amount and for a duration sufficient to reduce plasma AA levels by at least about 50 µg/mL, 55 µg/mL, 60 µg/mL, 65 µg/mL, even at least about 70 µg/mL, 75 µg/mL, 80 µg/mL, 85 µg/mL, 90 µg/mL, even at least about 95 µg/mL or 100 µg/mL.

In certain embodiments, the effective amount is at least about 2 g per day. In various embodiments, the effective amount is at least about 3 g per day. In particular embodiments, the effective amount is at least about 4 g per day. In typical embodiments, the effective amount is about 2 g per day. In certain embodiments, the effective amount is about 4 g per day.

In typical embodiments, the pharmaceutical composition is administered for at least 30 days. In certain embodiments, the pharmaceutical composition is administered for at least 60 days. In particular embodiments, the pharmaceutical composition is administered for at least 90 days, 120 days, 180 days, 240 days, or at least 360 days. In certain embodiments, the pharmaceutical composition is administered indefinitely.

In some embodiments, the pharmaceutical composition is administered daily. In other embodiments, the pharmaceutical composition is administered every other day.

In particular embodiments, the daily dosage of pharmaceutical composition is administered in a single daily dose. In other embodiments, the pharmaceutical composition is administered in divided doses, with the daily dose divided into two administrations, three administrations, or even four administrations, over the course of the day.

In certain embodiments, the pharmaceutical composition is administered with food. In certain embodiments, the pharmaceutical composition is administered with a low fat meal. In other embodiments, the pharmaceutical composition is administered without food. In certain embodiments, the pharmaceutical composition is administered in the fasting state.

5.6.2. Treatment of Hypertriglyceridemia (200-500 mg/dL)

In another series of treatment embodiments, methods are provided for treating patients who have pre-treatment serum or plasma triglyceride levels of about 200 mg/dL to about 500 mg/dL. In certain embodiments, the patients are already on statin therapy; in these patients, the pre-treatment serum or plasma triglyceride levels are those measured during statin treatment, prior to administration of the pharmaceutical compositions described herein.

The method comprises orally administering the pharmaceutical composition described herein to a patient having pre-treatment serum or plasma triglyceride levels of about 200 mg/dL to about 500 mg/dL, in an amount and for a duration effective to reduce serum or plasma triglycerides below pre-treatment levels.

In certain embodiments, the pharmaceutical composition described herein is administered in an amount and for a duration sufficient to reduce serum or plasma triglyceride levels by at least about 5% below pre-treatment levels. In various embodiments, the pharmaceutical composition is administered in an amount and for a duration sufficient to reduce serum or plasma triglyceride levels by at least about 6%, 7%, 8%, 9%, 10%, 11%, 12%, 13%, 14%, 15%, even at least about 16%, 17%, 18%, 19%, or at least about 20% below pre-treatment levels.

In some embodiments, the pharmaceutical composition described herein is administered in an amount and for a duration sufficient to reduce non-HDL-cholesterol by at least about 1%, at least about 2%, at least about 3%, 4%, 5%, even at least about 7%, 8%, 9%, or at least about 10% below pre-treatment levels. In certain embodiments, the pharmaceutical composition is administered in an amount and for a duration sufficient to reduce non-HDL-cholesterol by at least about 15%, at least about 20%, at least about 25%, at least about 30%, at least about 35%, at least about 40% below pre-treatment levels.

In a series of embodiments, the pharmaceutical composition is administered in an amount and for a duration sufficient to raise HDL-c levels by at least about 1%, 2%, 3%, 4%, 5%, 6%, 7%, even at least about 8%, 9%, or 10% or more above pre-treatment levels.

In some embodiments, the pharmaceutical composition is administered in an amount and for a duration effective to increase plasma EPA levels by at least 100% above pre-treatment levels. In certain embodiments, the pharmaceutical composition is administered in an amount and for a duration effective to increase plasma EPA levels by at least about 200%, 250%, 300%, even at least about 350%, 400%, 450% or at least about 500% above pre-treatment levels. In selected embodiments, the pharmaceutical composition is administered for a time and in an amount effective to increase plasma EPA levels by at least about 550%, 600%, 650%, even at least about 700% above pre-treatment levels.

In various embodiments, the pharmaceutical composition is administered in an amount and for a duration effective to increase plasma DHA levels by at least about 50% above pre-treatment levels. In particular embodiments, the pharmaceutical composition is administered in an amount and for a duration effective to increase plasma DHA levels by at least about 55%, 60%, 65%, 70%, even at least about 75%, 80%, 85%, or 90% above pre-treatment levels.

In a series of embodiments, the pharmaceutical composition is administered in an amount and for a duration effective to increase plasma DPA levels by at least about 50% above pre-treatment levels. In some embodiments, the pharmaceutical composition is administered in an amount and for a duration effective to increase plasma DPA levels by at least about 55%, 60%, 65%, 70%, 75%, even at least about 80%, 85%, 90%, 95%, or 100% above pre-treatment levels. In selected embodiments, the pharmaceutical composition is administered in an amount and for a duration effective to increase plasma DPA levels by at least about 110%, 120%, even at least about 125% above pre-treatment levels.

In a series of embodiments, the pharmaceutical composition is administered in an amount and for a duration effective to reduce arachidonic acid (AA) concentration in plasma by at least about 5% below pre-treatment levels. In certain embodiments, the pharmaceutical composition is administered in an amount and for a duration effective to reduce arachidonic (AA) concentration in plasma by at least about 6%, 7%, 8%, 9%, 10%, even at least about 11%, 12%, 13%, 14%, even at least about 15%, 16%, 17%, 18%, 19%, 20%, or 21%, 22%, 23%, 24% even at least about 25% below pre-treatment levels.

In certain embodiments, the pharmaceutical composition is administered in an amount, and for a duration, effect to reduce plasma arachidonic acid concentration by at least about 25 µg/mL. In some embodiments, the pharmaceutical composition is administered in an amount and for a duration sufficient to reduce plasma AA levels by at least about 50 µg/mL, 55 µg/mL, 60 µg/mL, 65 µg/mL, even at least about 70 µg/mL, 75 µg/mL, 80 µg/mL, 85 µg/mL, 90 µg/mL, even at least about 95 µg/mL or 100 µg/mL.

In various embodiments, the pharmaceutical composition described in Section 5.2 herein is administered in unit dosage forms as described in Section 5.3 above.

In various embodiments, the pharmaceutical composition is administered in an amount of at least about 1 g per day. In some embodiments, the pharmaceutical composition is administered in an amount of at least about 2 g/day. In certain embodiments, the pharmaceutical composition is administered in an amount of at least about 3 g/day. In particular embodiments, the pharmaceutical composition is administered in an amount of at least about 4 g/day. In typical embodiments, the pharmaceutical composition is administered in an amount of about 2 g/day. In certain embodiments, the pharmaceutical composition is administered in an amount of about 3 g/day or about 4 g per day.

5.6.3. Treatment of Primary Hyperlipidemia or Mixed Dyslipidemia

In a series of treatment embodiments, methods are provided for treating patients who have primary hyperlipidemia or mixed dyslipidemia. The method comprises orally administering the pharmaceutical composition described herein to a patient having primary hyperlipidemia or mixed dyslipidemia, in an amount and for a duration effective to reduce one or more of elevated total-cholesterol, elevated LDL-C, elevated ApoB, non-HDL-C, and elevated triglyceride levels, and/or to increase HDL-C.

In various embodiments, the pharmaceutical composition is administered in an amount of at least about 1 g per day. In some embodiments, the pharmaceutical composition is administered in an amount of at least about 2 g/day. In certain embodiments, the pharmaceutical composition is administered in an amount of at least about 3 g/day. In particular embodiments, the pharmaceutical composition is administered in an amount of at least about 4 g/day. In typical embodiments, the pharmaceutical composition is administered in an amount of about 2 g/day. In certain embodiments, the pharmaceutical composition is administered in an amount of about 3 g/day or about 4 g per day.

5.6.4. Treatment to Increase Plasma EPA:AA Ratios

Methods are also provided for increasing the EPA:AA ratio. The methods comprise administering the pharmaceutical composition described in Section 5.2 herein to a patient having an EPA:AA ratio below about 0.25, in an amount and for duration sufficient to increase the patient's EPA:AA ratio to at least about 0.25. In some embodiments, the pharmaceutical composition is administered in an amount and for a duration sufficient to increase the patient's EPA:AA ratio to at least about 0.3, at least about 0.35, at least about 0.40, at least about 0.45, at least about 0.50, even to a level of at least about 0.55, 0.60, 0.61, 0.62, 0.63, 0.64, or 0.65.

In certain embodiments, the method comprises administering the pharmaceutical composition in an amount and for a duration effective to increase plasma EPA levels by at least 100% above pre-treatment levels. In certain embodiments, the pharmaceutical composition is administered in an amount and for a duration effective to increase plasma EPA levels by at least about 200%, 250%, 300%, even at least about 350%, 400%, 450% or at least about 500% above pre-treatment levels. In selected embodiments, the pharmaceutical composition is administered for a time and in an amount effective to increase plasma EPA levels by at least about 550%, 600%, 650%, even at least about 700% above pre-treatment levels.

In various embodiments, the pharmaceutical composition is administered in an amount and for a duration effective to increase plasma DHA levels by at least about 50% above pre-treatment levels. In particular embodiments, the pharmaceutical composition is administered in an amount and for a duration effective to increase plasma DHA levels by at least about 55%, 60%, 65%, 70%, even at least about 75%, 80%, 85%, or 90% above pre-treatment levels.

In a series of embodiments, the pharmaceutical composition is administered in an amount and for a duration effective to reduce arachidonic acid (AA) concentration in plasma by at least about 5% below pre-treatment levels. In certain embodiments, the pharmaceutical composition is administered in an amount and for a duration effective to reduce arachidonic (AA) concentration in plasma by at least about 6%, 7%, 8%, 9%, 10%, even at least about 11%, 12%, 13%, 14%, even at least about 15%, 16%, 17%, 18%, 19%, 20%, or 21%, 22%, 23%, 24% even at least about 25% below pre-treatment levels.

In certain embodiments, the pharmaceutical composition is administered in an amount, and for a duration, effect to reduce plasma arachidonic acid concentration by at least about 25 μg/mL. In some embodiments, the pharmaceutical composition is administered in an amount and for a duration sufficient to reduce plasma AA levels by at least about 50 μg/mL, 55 μg/mL, 60 μg/mL, 65 μg/mL, even at least about 70 μg/mL, 75 μg/mL, 80 μg/mL, 85 μg/mL, 90 μg/mL, even at least about 95 μg/mL or 100 mg/mL.

In various embodiments, the pharmaceutical composition described in Section 5.2 herein is administered in unit dosage forms as described in Section 5.3 above.

In various embodiments, the pharmaceutical composition is administered in an amount of at least about 1 g per day. In some embodiments, the pharmaceutical composition is administered in an amount of at least about 2 g/day. In certain embodiments, the pharmaceutical composition is administered in an amount of at least about 3 g/day. In particular embodiments, the pharmaceutical composition is administered in an amount of at least about 4 g/day. In typical embodiments, the pharmaceutical composition is administered in an amount of about 2 g/day. In certain embodiments, the pharmaceutical composition is administered in an amount of about 3 g/day or about 4 g per day.

5.6.5. Treatment to Lower Serum or Plasma ApoCIII Levels

Methods are also provided for increasing a patient's serum or plasma ApoCIII levels, without regard to the patient's pre-treatment plasma triglyceride levels. The methods comprise administering the pharmaceutical composition described in Section 5.2 herein to a patient in need of lower ApoCIII levels, in an amount and for duration sufficient to decrease the patient's serum or plasma ApoCIII levels. In typical embodiments, the patient is at risk for cardiovascular heart disease.

In certain embodiments, the pharmaceutical composition is administered in an amount and for a duration sufficient to decrease ApoCIII levels by at least about 1%, 2%, 3%, 4%, 5%, 6%, 7%, even at least about 8%, 9% or 10% below pre-treatment levels.

5.6.6. Other Methods of Treatment

In another aspect, the pharmaceutical compositions described herein is used to treat other disorders, including one or more of nonalcoholic steatohepatitis (NASH), hyperlipoproteinemia, including type III hyperlipoproteinemia, and metabolic syndrome.

In certain embodiments, the pharmaceutical composition is used to reduce resistance to platelet aggregation inhibitors, such as Plavix, including use in the methods described in U.S. patent application Ser. No. 13/620,312, the disclosure of which is incorporated herein by reference in its entirety.

6. EXAMPLES

Example 1

Solubility of Statins in Various pH Buffers 50 mg of atorvastatin was added to 5 mL of water, 0.1N NaCl, 0.1N NaOH, 0.1N HCl (pH 1.2), acid phthalate buffer (pH 2.2), acid phthalate buffer (pH 4.0), neutralized phthalate buffer (pH 5.0), phosphate buffer (pH 7.0), or alkaline borate buffer (pH 9.0). The solutions were sonicated for 10 minutes and allowed to sit overnight. Aliquots of the sample solutions were centrifuged and an aliquot of the supernatant from each sample was assayed for atorvastatin solubility. Samples were then allowed to sit for 1 week when they were again assayed to determine atorvastatin solubility. The results of solubility measurements are displayed in Table 3.

50 mg of rosuvastatin was added to 5 mL of water, 0.1N NaCl, 0.1N NaOH, 0.1N HCl (pH 1.2), acid phthalate buffer (pH 2.2), acid phthalate buffer (pH 4.0), neutralized phthalate buffer (pH 5.0), phosphate buffer (pH 7.0), or alkaline borate buffer (pH 9.0). The solutions were sonicated for 10 minutes and allowed to sit overnight. Aliquots of the sample solutions were centrifuged and an aliquot of the supernatant from each sample was assayed for rosuvastatin solubility. Samples were then allowed to sit for 1 week when they were again assayed to determine rosuvastatin solubility. The results of solubility measurements are displayed in Table 3.

TABLE 3

Atorvastatin Calcium and Rosuvastatin Calcium Solubility Data

| | Atorvastatin | | Rosuvastatin | |
|---|---|---|---|---|
| Solution | T = 0 | T = 1 Week | T = 0 | T = 1 Week |
| Water | 0.146 | 0.138 | 7.08 | 8.822 |
| 0.1N HCl | 0.019 | 0.012 | 0.223 | 0.104 |
| pH 2.2 | 0.041 | 0.015 | 0.773 | 9.343 |
| pH 4.0 | 0.074 | 0.06 | 1.901 | 0.002 |
| pH 5.0 | 0.115 | 0.1 | 4.188 | 4.790 |
| pH 7.0 | 0.286 | 0.285 | 7.963 | 10.654 |
| pH 9.0 | 0.247 | 0.225 | 4.571 | 4.712 |
| 0.1N NaOH | 0.246 | 0.352 | 8.058 | 0.018 |

The results showed that Rosuvastatin displayed significant aqueous solubility at time zero, with the maximal solubility at about pH 7.0. Atorvastatin showed a lower overall aqueous solubility than rosuvastatin, but the solubility also displayed a maximum at pH 7.0.

Example 2

Solubility of Statins in PUFA Free Acid Solvent System

Samples of 20-30 mg of atorvastatin and 20-30 mg of rosuvastatin were each dissolved in 2 g of a PUFA free acid solvent system. The composition of the solvent system is given in Table 4, below (batch #37225).

TABLE 4

PUFA free acid solvent system (batch # 37225)

| Identity | Common name | area % |
|---|---|---|
| C18:2(n-6) | Linoleic acid | 0.59 |
| C18:3(n-6) | Gamma-linolenic acid | 0.12 |
| C18:3(n-3) | α-Linolenic acid | 0.38 |
| C18:4(n-3) | Moroctic acid | 1.16 |
| C20:2(n-6) | Eicosadienoic acid | 0.12 |
| C20:3(n-6) | Dihomo-gamma-linolenic acid | 0.45 |
| C20:4(n-6) | Arachidonic acid | 2.84 |
| C20:3(n-3) | Eicosatrienoic acid | 0.22 |
| C20:4(n-3) | Eicosatetraenoic acid | 2.11 |
| C20:5(n-3) | EPA | 55.81 |
| C21:5(n-3) | Heneicosapentaenoic acid | 2.72 |
| C22:5(n-6) | Docosapentaenoic acid | 0.72 |
| C22:5(n-3) | DPA | 5.46 |
| C22:6(n-3) | DHA | 19.45 |

Initial solubility was measured, and results of solubility measurement are displayed in Table 5.

TABLE 5

Initial solubility in PUFA free acid solvent system

| | Concentration (mg/mL) | |
|---|---|---|
| Solution | Atorvastatin | Rosuvastatin |
| PUFA free acid solvent system Batch #37225 | 7.85 | 12.70 |

Example 3

Solubility of Statins in Omega-3 Ethyl Ester Solvent System 20 mg of atorvastatin and 20 mg of rosuvastatin were each added to 2 g of fill extracted from capsules of Lovaza, in which the PUFA species are present substantially in the ethyl ester form. The samples were then sonicated for 1 hour and incubated overnight, after which they displayed excess un-dissolved solids. The samples were centrifuged and the supernatant assayed by HPLC for the respective statin. The results of the solubility measurement are displayed in Table 6. As is apparent from comparing Tables 5 and Table 6, atorvastatin and rosuvastatin were solubilized to a significantly greater extent in a PUFA free acid solvent system than in a PUFA ethyl ester solvent system.

TABLE 6

Initial solubility in PUFA ethyl ester solvent system

| | Concentration (mg/mL) | |
|---|---|---|
| Solution | Atorvastatin | Rosuvastatin |
| Lovaza | 0.005 | 0.001 |

Example 4

Comparison of Solubility and Stability of Statins Dissolved in Omega-3 Free Fatty Acids and Omega-3 Ethyl Esters Solubility of atorvastatin calcium, rosuvastatin calcium, simvastatin, pitavastatin calcium, and pravastatin sodium was evaluated in both a PUFA free acid solvent system (see Table 4) and a PUFA ethyl ester solvent system (Lovaza).

For this study, ten vials were prepared such that 5 vials contained 2 mL of Lovaza oil and 5 vials contained 2 mL of PUFA free acid solvent system. About 20 mg of each statin were added to one Lovaza oil vial and to one PUFA free acid solvent system vial. Vials containing the samples were blanketed with nitrogen, then sealed. The vials were then sonicated for 1 hour or until contents appeared clear. After sonication, vials which remained clear received additional 20 mg aliquots of their respective statin and were again blanketed with nitrogen. The process was repeated until all vials contained un-dissolved statin, with the exception of the pravastatin sodium in PUFA free acid solvent, which, after the addition of about 313 mg of pravastatin sodium, still remained clear. The samples were allowed to sit overnight, after which all samples were observed to contain un-dissolved statins. The samples were centrifuged and the supernatant was assayed for the respective statin by HPLC. Assay results are shown in Table 7 below.

TABLE 7

| Drug Substance | Solubility in Lovaza (ethyl ester) Solvent System (mg/g) | Solubility in PUFA Free Acid Solvent System (mg/g) |
|---|---|---|
| Atorvastatin Calcium | 0.005 | 7.850 |
| Rosuvastatin Calcium | 0.001 | 12.700 |
| Simvastatin | 19.267 | 45.783 |
| Pitavastatin Calcium | 0.615 | 12.771 |
| Pravastatin Sodium | 0.000 | 42.357 |

All of the tested statins displayed markedly higher solubility in the PUFA free fatty solvent system as compared to the PUFA ethyl ester solvent system.

Example 5

Stability Testing of Statins Dissolved in Omega-3 Free Fatty Acids

The stability of atorvastatin calcium and rosuvastatin calcium solubilized in a PUFA free acid solvent system was evaluated over the course of four weeks under 25° C., 60% relative humidity (RH) storage conditions.

Three batch formulations were prepared in parallel, by adding a sufficient amount of PUFA free acid solvent system to (i) 2.0 g of atorvastatin calcium, (ii) 2.0 g of rosuvastatin calcium, and (iii) no statin (control), to fill a 200 mL vessel, followed by blanketing of the solution with nitrogen and capping of the vessel. The compositions were then mixed until full dissolution was observed, using a magnetic stir bar and sonication for 30-60 second intervals, taking care to maintain a nitrogen headspace over the solution throughout processing.

Each statin-solvent system solution and the control solvent system were each respectively aliquoted into nine separate 20 mL Type I borosilicate vials, which were then blanketed with nitrogen, capped with a Teflon-coated serum stopper, and crimp sealed. Vials were covered with foil to protect from light and stored at 25° C., 60% RH.

One vial of each of the three compositions was retrieved at each timepoint for testing. Procedures as listed in the USP Monograph for Omega-3-Acid Ethyl Ester Capsules were followed for measuring quantities of acid value, peroxide value, and absorbance for fats and fixed oils. The results are shown in Tables 8 and 9, below.

TABLE 8

Stability Testing for Atorvastatin Dissolved in PUFA free acid solvent system

| Statin in Oil | t = 0 | | t = 1 week | | t = 2 week | |
|---|---|---|---|---|---|---|
| | mg/g | Percent | mg/g | Percent | mg/g | Percent |
| Atorvastatin Peak 1 | 3.659 | 41.87 | 1.632 | 19.72 | 1.509 | 19.25 |
| Atorvastatin Peak 2 | 5.079 | 58.13 | 6.643 | 80.28 | 6.330 | 80.75 |
| Total | 8.738 | 100 | 8.275 | 100 | 7.839 | 100 |

TABLE 9

Stability Testing for Atorvastatin Dissolved in PUFA free acid solvent system

| Statins in Oil | t = 0 | | t = 1 week | | t = 2 week | |
|---|---|---|---|---|---|---|
| | mg/g | Percent | mg/g | Percent | mg/g | Percent |
| Rosuvastatin Peak 1 | 4.696 | 72.46 | 2.019 | 31.47 | 1.824 | 28.04 |
| Rosuvastatin Peak 2 | 1.785 | 27.54 | 4.397 | 68.53 | 4.681 | 71.96 |
| Total | 6.481 | 100 | 6.416 | 100 | 6.505 | 100 |

After pH adjustment, the two peaks were shown to reduce to a single peak of intact statin. No significant degradation was observed.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. A pharmaceutical composition comprising a statin dissolved in a polyunsaturated fatty acid ("PUFA") free acid solvent system, wherein the PUFA free acid solvent system comprises:
    45% to 65% eicosapentaenoic acid ("EPA") by weight;
    15% to 25% docosahexaenoic acid ("DHA") by weight; and
    1% to 8% docosapentaenoic acid ("DPA") (C22:5 n-3) by weight.

2. The pharmaceutical composition according to claim 1, wherein no more than about 10% by weight of the statin is undissolved in the solvent system.

3. The pharmaceutical composition according to claim 1, wherein the statin is dissolved in the PUFA free acid solvent system at a concentration of at least about 5 mg statin per gram solvent system.

4. The pharmaceutical composition according to claim 3, wherein the statin is dissolved in the PUFA free acid solvent system at a concentration of at least about 10 mg statin per gram solvent system.

5. The pharmaceutical composition according to claim 4, wherein the statin is dissolved in the PUFA free acid solvent system at a concentration of at least about 20 mg statin per gram solvent system.

6. The pharmaceutical composition according to claim 1, wherein the statin is selected from the group consisting of: pravastatin, lovastatin, simvastatin, atorvastatin, fluvastatin, rosuvastatin, and pitavastatin.

7. An oral unit dosage form, wherein the dosage form comprises a capsule, the capsule containing a pharmaceutical composition according to claim 1.

8. The oral unit dosage form according to claim 7, wherein the capsule comprises gelatin.

9. The oral unit dosage form according to claim 8, wherein the capsule is a soft gelatin capsule.

10. The oral unit dosage form of claim 9, wherein the soft gelatin capsule comprises Type A gelatin.

11. The oral unit dosage form of claim 10, wherein the type A gelatin is porcine type A gelatin.

12. The oral unit dosage form of claim 7, further comprising a coating on the exterior of the capsule.

13. The oral unit dosage form according to claim 12, wherein the coating is a pH-insensitive coating.

14. The oral unit dosage form according to claim 13, wherein the coating is a poly(ethylacrylate-methylacrylate) copolymer.

15. The oral unit dosage form according to claim 7, wherein the capsule contains about 1 to about 100 mg of a statin dissolved in about 500 mg to about 1 g of a PUFA free acid solvent system.

16. The oral unit dosage form according to claim 15, wherein the capsule contains about 2.5 mg to about 40 mg of a statin dissolved in about 1 g of a PUFA free acid solvent system.

17. A method of treating a blood lipid disorder, comprising administering a pharmaceutical composition according to claim 1 to a subject with a blood lipid disorder in an amount and for a duration sufficient to treat the blood lipid disorder.

18. The method according to claim 17, wherein the blood lipid disorder is selected from the group consisting of: hypertriglyceridemia, hyperlipidemia, hypercholesterolemia, mixed dyslipidemia, and atherosclerosis.

19. The method according to claim 17, wherein the method comprises administering at least 2 g of the pharmaceutical composition daily.

20. The pharmaceutical composition according to claim 1, wherein the statin is selected from atorvastatin, rosuvastatin, simvastatin, pitavastatin, and pravastatin.

21. The pharmaceutical composition according to claim 1, wherein the statin is rosuvastatin.

22. The pharmaceutical composition according to claim 1, wherein the composition does not include a surfactant.

23. The method according to claim 17, wherein the statin in the pharmaceutical composition is selected from atorvastatin, rosuvastatin, simvastatin, pitavastatin, and pravastatin.

24. The method according to claim 17, wherein the statin in the pharmaceutical composition is rosuvastatin.

25. The pharmaceutical composition according to claim 1, wherein the PUFA free acid solvent system further comprises moroctic acid, arachidonic acid, eicosatetraenoic acid, or heneicosapentaenoic acid.

26. The pharmaceutical composition according to claim 1, wherein the PUFA free acid solvent system further comprises moroctic acid, arachidonic acid, eicosatetraenoic acid, and heneicosapentaenoic acid.

27. The pharmaceutical composition according to claim 1, wherein the PUFA free acid solvent system further comprises:
　　0.81% to 2.31% moroctic acid by weight;
　　1.41% to 4.87% arachidonic acid by weight;
　　1.46% to 2.92% eicosatetraenoic acid by weight; or
　　1.85% to 3.37% heneicosapentaenoic acid by weight.

28. The pharmaceutical composition according to claim 1, wherein the PUFA free acid solvent system further comprises:
　　0.81% to 2.31% moroctic acid by weight;
　　1.41% to 4.87% arachidonic acid by weight;
　　1.46% to 2.92% eicosatetraenoic acid by weight; and
　　1.85% to 3.37% heneicosapentaenoic acid by weight.

29. The pharmaceutical composition according to claim 1, wherein the PUFA free acid solvent system comprises 20% or less non-PUFA solubilizers by weight.

30. The pharmaceutical composition according to claim 1, wherein the PUFA free acid solvent system comprises 10% or less non-PUFA solubilizers by weight.

31. A pharmaceutical composition comprising a statin dissolved in a polyunsaturated fatty acid ("PUFA") free acid solvent system, wherein the PUFA free acid solvent system comprises:
　　45% to 65% eicosapentaenoic acid ("EPA") by weight;
　　15% to 25% docosahexaenoic acid ("DHA") by weight;
　　1% to 8% docosapentaenoic acid ("DPA") (C22:5 n-3) by weight;
　　0.81% to 2.31% moroctic acid by weight;
　　1.41% to 4.87% arachidonic acid by weight;
　　1.46% to 2.92% eicosatetraenoic acid by weight; and
　　1.85% to 3.37% heneicosapentaenoic acid by weight;
　　wherein the statin is selected from atorvastatin, rosuvastatin, simvastatin, pitavastatin, and pravastatin.

32. The pharmaceutical composition according to claim 31, wherein the statin is rosuvastatin.

* * * * *